(12) United States Patent
Satoh

(10) Patent No.: US 8,206,301 B2
(45) Date of Patent: Jun. 26, 2012

(54) ULTRASONIC IMAGING APPARATUS AND ULTRASONIC IMAGE PROCESSING APPARATUS, METHOD AND PROGRAM

(75) Inventor: Yoshiaki Satoh, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 1852 days.

(21) Appl. No.: 11/339,807

(22) Filed: Jan. 26, 2006

(65) Prior Publication Data

US 2006/0184023 A1    Aug. 17, 2006

(30) Foreign Application Priority Data

Feb. 1, 2005   (JP) .................................. 2005-024758
Mar. 31, 2005  (JP) .................................. 2005-102792

(51) Int. Cl.
*A61B 8/00*     (2006.01)
(52) U.S. Cl. ........ 600/443; 600/407; 600/437; 600/444; 382/128
(58) Field of Classification Search .................. 600/443, 600/465, 437, 407, 501
See application file for complete search history.

(56) References Cited

U.S. PATENT DOCUMENTS

| | | | | | |
|---|---|---|---|---|---|
| 4,790,321 | A | * | 12/1988 | Miwa et al. ................... | 600/443 |
| 5,782,768 | A | * | 7/1998 | Hashimoto et al. ........... | 600/443 |
| 6,035,071 | A | * | 3/2000 | Yamada ......................... | 382/263 |
| 6,068,597 | A | * | 5/2000 | Lin ................................ | 600/443 |
| 6,373,970 | B1 | * | 4/2002 | Dong et al. ..................... | 382/128 |
| 6,535,651 | B1 | * | 3/2003 | Aoyama et al. ................ | 382/300 |
| 2002/0028994 | A1 | * | 3/2002 | Kamiyama ..................... | 600/437 |
| 2002/0123688 | A1 | * | 9/2002 | Yamauchi ....................... | 600/443 |
| 2003/0007702 | A1 | * | 1/2003 | Aoyama et al. ................ | 382/300 |
| 2003/0161520 | A1 | * | 8/2003 | Yamano et al. ................ | 382/128 |
| 2003/0169946 | A1 | * | 9/2003 | Bamford et al. ............... | 382/308 |
| 2003/0228061 | A1 | * | 12/2003 | Sakuyama ..................... | 382/233 |
| 2004/0077946 | A1 | * | 4/2004 | Ohmiya ......................... | 600/437 |
| 2004/0091145 | A1 | * | 5/2004 | Kohashi et al. ................ | 382/162 |

FOREIGN PATENT DOCUMENTS

| JP | 2003-061964 A | 3/2003 |
|---|---|---|
| JP | 2004-041617 A | 2/2004 |

OTHER PUBLICATIONS

Kamiyama, et al., "Tissue Characterization Using Statistical Information from Ultrasound Echo Signals", Medical Imaging Technology vol. 21, No. 2, p. 112-p. 116, Mar. 2003.

* cited by examiner

*Primary Examiner* — Tse Chen
*Assistant Examiner* — Joel F Brutus
(74) *Attorney, Agent, or Firm* — Sughrue Mion, PLLC

(57) ABSTRACT

An ultrasonic image processing apparatus capable of analyzing speckle information contained in the entire ultrasonic image and displaying the analysis results as a moving image. The ultrasonic image processing apparatus is an apparatus for processing reception signals, which are obtained by transmitting ultrasonic waves toward an object to be inspected and receiving ultrasonic echoes from the object, to generate ultrasonic image data, and the apparatus includes: a speckle image generating unit for generating speckle image data representing a speckle image based on original data generated by performing signal processing on the reception signals and representing ultrasonic image information on the object; and a speckle image analysis unit for performing analysis of the speckle images represented by the speckle image data generated by the speckle image generating unit to generate speckle analysis result image data representing analysis results as a moving image.

31 Claims, 31 Drawing Sheets

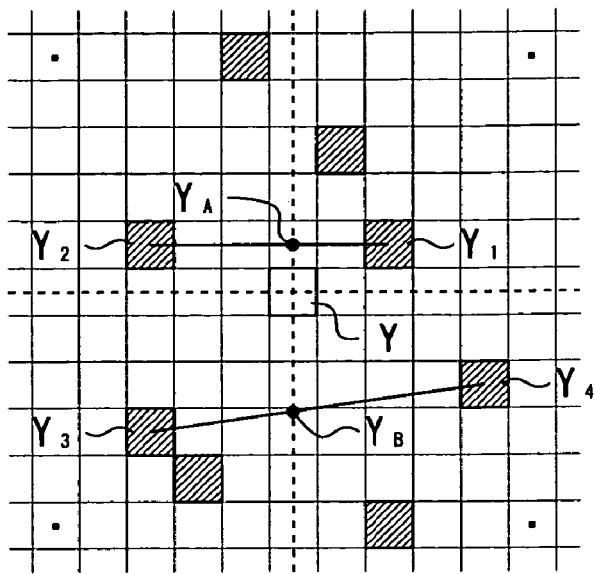 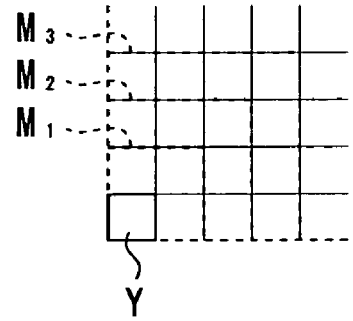
*FIG.16A*  *FIG.16B*
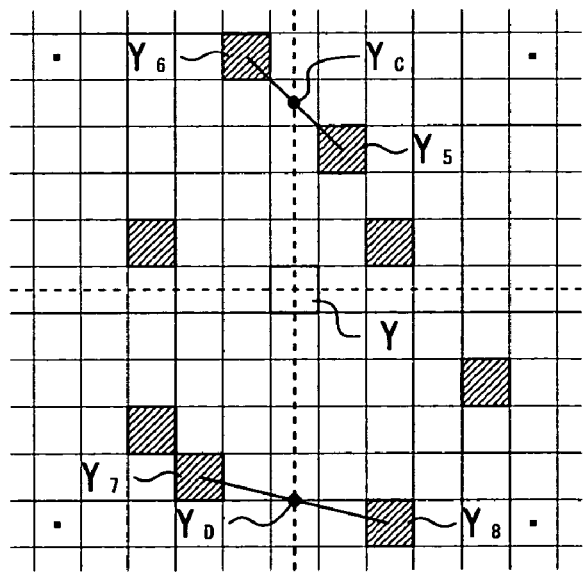 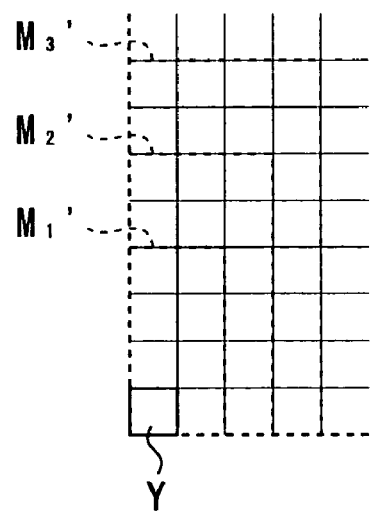
*FIG.17A*  *FIG.17B*

ULTRASONIC IMAGING APPARATUS AND ULTRASONIC IMAGE PROCESSING APPARATUS, METHOD AND PROGRAM

BACKGROUND OF THE INVENTION

1. Field of the Invention

The present invention relates to an ultrasonic imaging apparatus for generating ultrasonic images based on reception signals obtained by transmitting ultrasonic waves and receiving ultrasonic echoes, and an ultrasonic image processing apparatus for processing image data in such an ultrasonic imaging apparatus. Further, the present invention relates to an ultrasonic image processing method and an ultrasonic image processing program to be used in such an ultrasonic image processing apparatus.

2. Description of a Related Art

In medical fields, various imaging technologies have been developed in order to observe the interior of an object to be inspected and make diagnoses. Especially, ultrasonic imaging for obtaining interior information of the object by transmitting and receiving ultrasonic waves enables image observation in real time and provides no exposure to radiation unlike other medical image technologies such as X-ray photography or RI (radio isotope) scintillation camera. Accordingly, ultrasonic imaging is utilized as an imaging technology at a high level of safety in a wide band of departments including not only the fetal diagnosis in the obstetrics, but also gynecology, circulatory system, digestive system, etc.

The ultrasonic imaging is an image generation technology utilizing the nature of ultrasonic waves that they are reflected at a boundary between regions with different acoustic impedances (e.g., a boundary between structures). Therefore, the outline of a structure (e.g., internal organs, diseased tissues, or the like) existing within an object to be inspected such as a human body can be extracted by transmitting an ultrasonic beam into the object, receiving ultrasonic echoes generated within the object, and obtaining reflection points, where the ultrasonic echoes are generated, and the reflection intensity.

By the way, in an ultrasonic image in which an object having a nonuniform structure like a living body is imaged, a pattern, in which bright parts and/or dark parts are scattered, appears. Such a pattern is called a speckle pattern, and generated, for example, by interference between ultrasonic echoes reflected by nonuniform tissues existing within an internal organ or the like. This speckle pattern is a kind of virtual image, and thereby, the detected outline of the structure or the like often becomes unclear.

Japanese Patent Application Publication JP-P2003-61964A discloses an ultrasonic diagnostic apparatus for smoothing images by utilizing statistical characteristics of a speckle pattern and extracting minute structures to observe minute abnormal lesions within a homogeneous tissue structure such as the stage of liver cirrhosis progression. This ultrasonic diagnostic apparatus includes analysis calculation means for extracting a particular signal by using intensity of echo signals generated from a part of an object to be inspected or the statistical characteristics of amplitude information, and display means for displaying a result extracted by the analysis calculation means (page 1, FIG. 1).

Further, Japanese Patent Application Publication JP-P2004-41617A discloses an ultrasonic diagnostic apparatus usable for tissue diagnoses by quantifying the fineness of a speckle pattern contained in an ultrasonic image. This ultrasonic diagnostic apparatus includes image forming means for forming an ultrasonic image based on echo data obtained by transmitting and receiving ultrasonic waves, binarization processing means for generating plural binarized images by performing binarization processing on the ultrasonic image while varying threshold levels, region factor means for obtaining the number of independent regions having high brightness or low brightness by performing labeling processing with respect to each of the binarized images, and graph creating means for creating a speckle evaluation graph representing the number of individual regions at each of the threshold level (page 1). According to this ultrasonic diagnostic apparatus, since the created speckle evaluation graph reflects tissue properties, tissue diagnoses can be made by performing numerical analysis on the graph. Further, JP-P2004-41617A also discloses that processing of emphasizing speckles (processing of removing base components) is performed prior to binarization processing, and that an image before binarization and an image after binarization are simultaneously displayed.

Further, in Kamiyama et al., "Tissue Characterization Using Statistical Information from Ultrasound Echo Signals", MEDICAL IMAGING TECHNOLOGY, Vol. 21, No. 2, March 2003, pp. 112-116, the general characteristics and statistical characteristics of a speckle pattern appearing in an ultrasonic tomographic image is described and study on tissue property diagnoses utilizing such statistical characteristics of the ultrasonic signal is introduced.

As described above, in ultrasonic diagnoses, speckles appearing in ultrasonic images are extracted, analyzed and displayed according to diagnostic purposes. Since it is considered that spackles contain information relating to tissue properties, it can be usable for diagnoses of tissue properties to extract and display the speckles. However, the ultrasonic diagnostic apparatuses disclosed in JP-P2003-61964A and JP-P2004-41617A are for analysis within a preset region of interest and for displaying still images of speckles. In order to further effectively utilize the information relating to the tissue properties contained in the speckles, it is desirable that speckle information contained in the entire ultrasonic image can be analyzed and the analysis results can be displayed as a moving image. Also, it is considered that users desire such a function.

Here, as described in Kamiyama, et al., it is conceivable that the spatial frequency components of a speckle pattern become relatively high in an ultrasonic image because the speckle pattern is produced by interference between ultrasonic waves. Accordingly, if an ultrasonic image in a specific relatively high frequency band can be displayed as a moving image, it would lead to extracting the speckle pattern easier and supporting diagnosis of tissue properties. However, in the present circumstances, no ultrasonic imaging apparatus having such a function has been proposed.

SUMMARY OF THE INVENTION

The present invention is achieved in view of the above-mentioned problems. The first purpose of the present invention is to provide an ultrasonic imaging apparatus, an ultrasonic image processing apparatus, an ultrasonic image processing method and an ultrasonic image processing program capable of analyzing speckle information contained in the entire ultrasonic image and displaying the analysis results as a moving image. Further, the second purpose of the present invention is to provide an ultrasonic imaging apparatus, an ultrasonic image processing apparatus, an ultrasonic image processing method and an ultrasonic image processing program capable of extracting a speckle pattern by displaying an ultrasonic image, which has spatial frequencies restricted in a relatively high band, as a moving image.

In order to solve the above-mentioned problems, an ultrasonic imaging apparatus according to a first aspect of the present invention is an ultrasonic imaging apparatus for transmitting ultrasonic waves toward an object to be inspected and receiving ultrasonic echoes from the object to display an ultrasonic image based on the received ultrasonic echoes, and the apparatus includes: ultrasonic transmitting means for transmitting ultrasonic waves according to applied drive signals; ultrasonic receiving means for receiving ultrasonic echoes generated by reflection of the ultrasonic waves transmitted from the ultrasonic transmitting means in the object to output reception signals; signal processing means for performing signal processing on the reception signals outputted from the ultrasonic receiving means to generate original data representing ultrasonic image information on the object; speckle image generating means for generating speckle image data representing a speckle image based on the original data generated by the signal processing means; and speckle image analysis means for performing analysis of the speckle image represented by the speckle image data generated by the speckle image generating means to generate speckle analysis result image data representing analysis results as a moving image.

Further, an ultrasonic imaging apparatus according to a second aspect of the present invention is an ultrasonic imaging apparatus for transmitting ultrasonic waves toward an object to be inspected and receiving ultrasonic echoes from the object to display an ultrasonic image based on the received ultrasonic echoes, and the apparatus includes: ultrasonic transmitting means for transmitting ultrasonic waves according to applied drive signals; ultrasonic receiving means for receiving ultrasonic echoes generated by reflection of the ultrasonic waves transmitted from the ultrasonic transmitting means in the object to output reception signals; signal processing means for performing signal processing on the reception signals outputted from the ultrasonic receiving means to generate image data representing ultrasonic image information on the object; band limited image data generating means for generating band limited image data representing a band limited image in which a spatial frequency band thereof is limited to a range not less than a center frequency of a spatial frequency band of an ultrasonic image represented by the image data generated by the signal processing means.

An ultrasonic image processing apparatus according to a first aspect of the present invention is an ultrasonic image processing apparatus for processing reception signals, which are obtained by transmitting ultrasonic waves toward an object to be inspected and receiving ultrasonic echoes from the object, to generate ultrasonic image data, and the apparatus includes: speckle image generating means for generating speckle image data representing a speckle image based on original data generated by performing signal processing on the reception signals and representing ultrasonic image information on the object; and speckle image analysis means for performing analysis of the speckle image represented by the speckle image data generated by the speckle image generating means to generate speckle analysis result image data representing analysis results as a moving image.

Further, an ultrasonic image processing apparatus according to a second aspect of the present invention is an ultrasonic image processing apparatus for processing reception signals, which are obtained by transmitting ultrasonic waves toward an object to be inspected and receiving ultrasonic echoes from the object, to generate ultrasonic image data, and the apparatus includes: band limited image data generating means for generating band limited image data representing a band limited image in which a spatial frequency band thereof is limited to a range not less than a center frequency of a spatial frequency band of an ultrasonic image represented by image data generated by performing signal processing on the reception signals and representing ultrasonic image information on the object; and a digital scan converter for converting a scan format with respect to the band limited image data to generate band limited image data for display.

An ultrasonic image processing method according to a first aspect of the present invention is an ultrasonic image processing method of processing reception signals, which are obtained by transmitting ultrasonic waves toward an object to be inspected and receiving ultrasonic echoes from the object, to generate ultrasonic image data, and the method includes the steps of: (a) generating speckle image data representing a speckle image based on original data generated by performing signal processing on the reception signals and representing ultrasonic image information on the object; and (b) performing analysis of the speckle image represented by the speckle image data generated at step (a) to generate speckle analysis result image data representing analysis results as a moving image.

An ultrasonic image processing method according to a second aspect of the present invention is an ultrasonic image processing method of processing reception signals, which are obtained by transmitting ultrasonic waves toward an object to be inspected and receiving ultrasonic echoes from the object, to generate ultrasonic image data, and the method includes the steps of: (a) performing signal processing on the reception signals obtained by receiving the ultrasonic echoes to generate image data representing ultrasonic image information on the object; and (b) generating band limited image data representing a band limited image in which a spatial frequency band thereof is limited to a range not less than a center frequency of a spatial frequency band of an ultrasonic image represented by the image data generated at step (a).

An ultrasonic image processing program according to a first aspect of the present invention is an ultrasonic image processing program for processing reception signals, which are obtained by transmitting ultrasonic waves toward an object to be inspected and receiving ultrasonic echoes from the object, to generate ultrasonic image data, and the program actuates a CPU to execute the procedures of: (a) generating speckle image data representing a speckle image based on original data generated by performing signal processing on the reception signals and representing ultrasonic image information on the object; and (b) performing analysis of the speckle image represented by the speckle image data generated at procedure (a) to generate speckle analysis result image data representing analysis results as a moving image.

An ultrasonic image processing program according to a second aspect of the present invention is an ultrasonic image processing program for processing reception signals, which are obtained by transmitting ultrasonic waves toward an object to be inspected and receiving ultrasonic echoes from the object, to generate ultrasonic image data, and the program actuates a CPU to execute the procedures of: (a) performing signal processing on the reception signals obtained by receiving the ultrasonic echoes to generate image data representing ultrasonic image information on the object; and (b) generating band limited image data representing a band limited image in which a spatial frequency band thereof is limited to a range not less than a center frequency of a spatial frequency band of an ultrasonic image represented by the image data generated at procedure (a).

According to the first aspect of the present invention, since a speckle analysis result image is generated by analyzing a spackle image and displayed as a moving image, medical diagnoses by doctors are facilitated and the diagnostic efficiency can be raised, and thereby, the quality of medical diagnoses can be improved. Further, according to the second aspect of the present invention, since a band limited image in which spatial frequencies are limited to a higher band than those of normal ultrasonic images is generated, spackle patterns generally having high spatial frequencies can be displayed in an easily viewable condition. Therefore, in the case where tissue properties of a part to be observed are determined based on speckle patterns, the ultrasonic imaging apparatus etc. having such a function can be utilized for effective diagnostic support.

BRIEF DESCRIPTION OF THE DRAWINGS

FIGS. 16A and 16B are diagrams for explanation of a method of performing four-point interpolation using square interpolation masks;

FIGS. 17A and 17B are diagrams for explanation of a method of performing four-point interpolation using flat interpolation masks;

DESCRIPTION OF THE PREFERRED EMBODIMENTS

Figure 1:
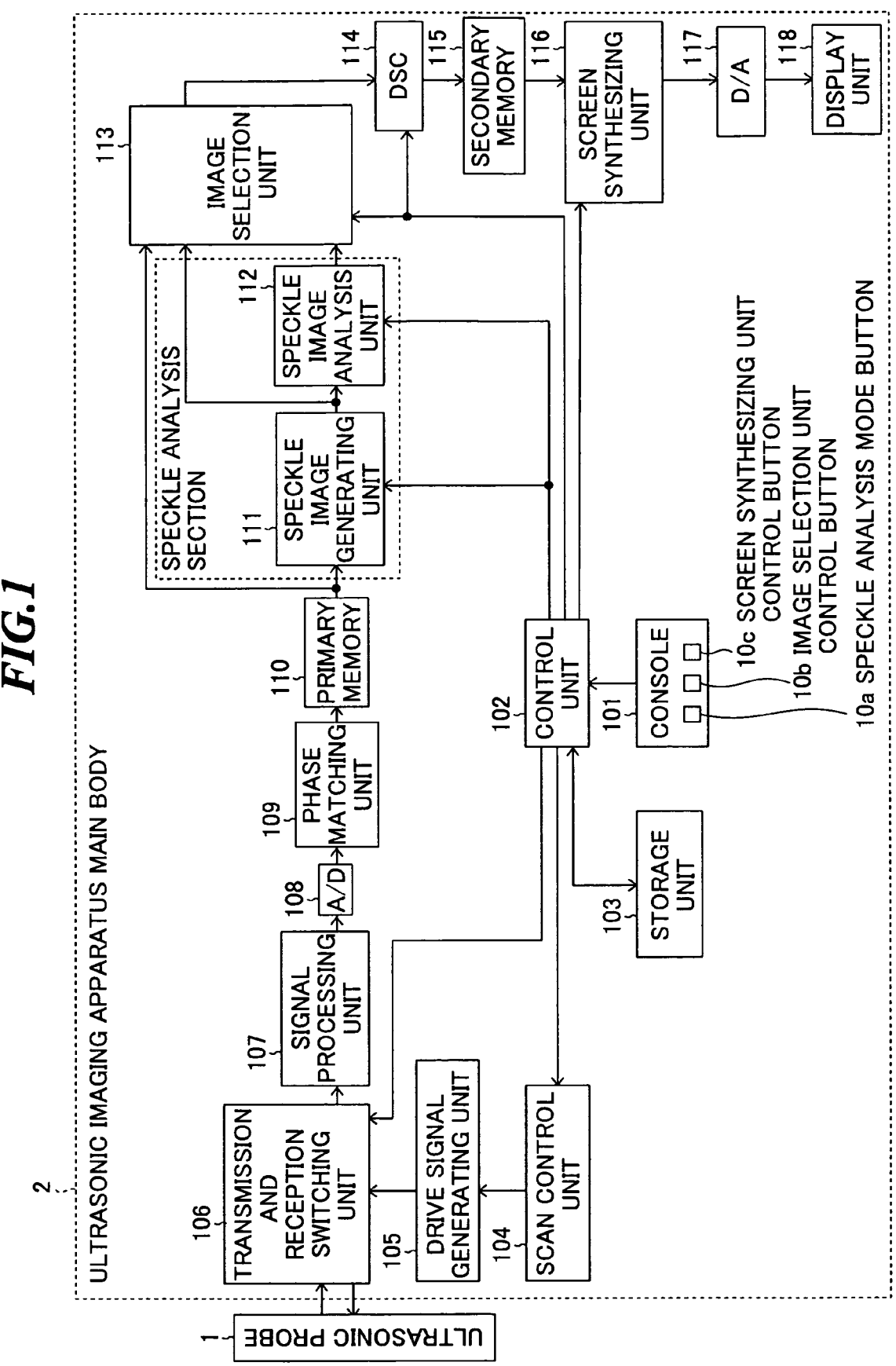
FIG. 1 is a block diagram showing a constitution of an ultrasonic imaging apparatus according to the first embodiment of the present invention.

Hereinafter, embodiments of the present invention will be described in detail by referring to the drawings. The same reference numbers will be assigned to the same component elements and the description thereof will be omitted.

FIG. 1 is a block diagram showing a constitution of an ultrasonic imaging apparatus according to the first embodiment of the present invention. This ultrasonic imaging apparatus includes an ultrasonic probe 1 for transmitting ultrasonic waves and receiving ultrasonic echoes, and an ultrasonic imaging apparatus main body 2 for controlling the transmission and reception of ultrasonic waves and generating an ultrasonic image based on reception signals obtained by detecting the ultrasonic echoes.

The ultrasonic probe 1 includes an ultrasonic transducer array in which plural ultrasonic transducers are arranged. Each ultrasonic transducer is fabricated by forming electrodes on both ends of a material having a piezoelectric property (piezoelectric material) such as a piezoelectric ceramic represented by PZT (Pb (lead) zirconate titanate) or a polymeric piezoelectric element represented by PVDF (polyvinylidene difluoride). When a voltage is applied to the electrodes of such an ultrasonic transducer by sending pulse electric signals or continuous wave electric signals, the piezoelectric material expands and contracts to generate ultrasonic waves. Accordingly, by electronically controlling plural ultrasonic transducers, pulse or continuous ultrasonic waves are generated from the ultrasonic transducers. Thereby, an ultrasonic beam is formed by combining those ultrasonic waves and an object to be inspected is electronically scanned. Further, the plural ultrasonic transducers expand and contract by receiving the propagating ultrasonic waves and generate electric signals. These electric signals are outputted as reception signals of the ultrasonic waves. Such an ultrasonic probe 1 is connected to the ultrasonic imaging apparatus main body 2 via a cable.

As the ultrasonic probe 1, a linear array probe in which plural ultrasonic transducers are arranged in one-dimensional manner, a sector probe that can sector-scan within the object, a convex array probe in which plural ultrasonic transducers are arranged on a convex surface, or the like is used. Further, a two-dimensional array probe in which plural ultrasonic transducers are arranged in a two-dimensional manner may be used. In this case, ultrasonic image on plural different sections can be obtained without mechanically moving the ultrasonic probe. Alternatively, as the ultrasonic probe 1, a probe within body cavity to be inserted into the object for performing ultrasonic imaging may be used. As the probe within body cavity, an ultrasonic probe to be used by being inserted into a treatment tool insertion hole of an endoscope, and an ultrasonic endoscope integrated with an endoscope is known. In the probe within body cavity, ultrasonic imaging is generally performed by a radial scan method. The radial scan method includes a mechanical radial scan method of transmitting and receiving ultrasonic waves while rotating the probe and imaging ultrasonic signals in synchronization with the rotation and an electronic radial scan method of scanning by electrically controlling plural transducers circularly arranged. By such scan methods, 360-degree surrounding region of the probe can be displayed at a time. Alternatively, as a probe within body cavity using another scan method other than the radial scan, one provided with a convex array at the tip end thereof is known.

Referring to FIG. 1, the ultrasonic imaging apparatus main body 2 includes a console 101, a control unit 102, a storage unit 103, a scan control unit 104, a drive signal generating unit 105, a transmission and reception switching unit 106, a signal processing unit 107, an A/D (analog/digital) converter 108, a phase matching unit 109, a primary memory 110, a speckle analysis section including a speckle image generating unit 111 and a speckle image analysis unit 112, an image selection unit 113, a DSC (digital scan converter) 114, a secondary memory 115, a screen synthesizing unit 116, a D/A (digital/analog) converter 117 and a display unit 118.

Among these units, at least the control unit 102, the speckle analysis section including the speckle image generating unit 111 and the speckle image analysis unit 112, the image selection unit 113, and the DSC 114 form an ultrasonic image processing apparatus according to the embodiment. Further, the ultrasonic image processing apparatus may further include the screen synthesizing unit 116.

The console 101 is used by a user when various instructions and information are inputted to the ultrasonic imaging apparatus main body. The console 101 includes an input device such as a keyboard and touch panel, a pointing device such as a mouse, an adjustment knob, an input button, etc. Further, the console 101 is provided with a speckle analysis mode button 10a for instructing the start of speckle analysis in the speckle analysis section, an image selection unit control button 10b for instructing image selection in the image selection unit 113, and a screen synthesizing unit control button 10c for instructing to select one of a synthesized image and a side-by-side image or select one of side-by-side image modes in the screen synthesizing unit 116.

The control unit 102 includes a CPU and software and controls the respective units of the ultrasonic imaging apparatus.

The storage unit 103 controls a recording medium for recording a fundamental program (software) for actuating the CPU included in the ultrasonic imaging apparatus to perform operation, and programs for performing various kinds of processing, and information to be used for those processing, etc. As the recording medium, not only the built-in hard disk, an external hard disk, a flexible disk, an MO, an MT, a RAM, a CD-ROM, a DVD-ROM, or the like may be used.

The scan control unit 104 is controlled to start and stop the operation by the control unit 102, and sets delay times provided to drive signals for driving the plural ultrasonic transducers included in the ultrasonic probe 1 according to directions in which ultrasonic waves are transmitted. Further, when a mechanical radial probe is used as the ultrasonic probe 1, the scan control unit 104 controls the motion of a motor for rotating the probe and controls the transmission directions of ultrasonic waves in synchronization with the motion.

The drive signal generating unit 105 includes plural pulsers corresponding to the plural ultrasonic transducers included in the ultrasonic probe 1. Each pulser generates a drive signal with predetermined timing under the control by the scan control unit 104. Thereby, ultrasonic waves are respectively generated from the plural ultrasonic transducers with predetermined time difference.

The transmission and reception switching unit 106 switches between input of the drive signals generated in the drive signal generating unit 105 to the ultrasonic probe 1 and load of reception signals in the signal processing unit 107, which will be described later, with predetermined timing under the control by the control unit 102. Thus, by limiting the time period for reading reception signals, ultrasonic echo signals reflected from a specific depth of the object are detected.

The signal processing unit 107 includes plural channels corresponding to the plural ultrasonic transducers. Each of these channels loads a reception signal outputted from the corresponding ultrasonic transducer with predetermined timing and performs signal processing such as amplification, Nyquist filter processing and so on.

The A/D converter 108 generates reception data by digitally converting analog signals processed in the signal processing unit 107.

The phase matching unit 109 performs reception focus processing by providing delays to the digitally converted plural reception data and adding them. Thereby, reception data (sound ray data) representing a reception beam having a focal point narrowed in the predetermined sound ray direction is generated. By further performing detection with respect to waveforms represented by the sound ray data, image data representing brightness values in plural pixels that form the ultrasonic image is obtained. Hereinafter, this image data is also referred to as "original data".

The primary memory 110 sequentially stores image data (original data) generated in the phase matching unit 109. The original data includes information on a structure within the object and information on a speckle pattern.

The speckle image generating unit 111 generates speckle image data frame by frame based on the original data read out from the primary memory 110 under the control of the control unit 102. Further, the speckle image analysis unit 112 analyses the speckle image represented by the speckle image data generated in the speckle image generating unit 111 and generates speckle analysis result image data representing the analysis result under the control of the control unit 102.

Figure 2:
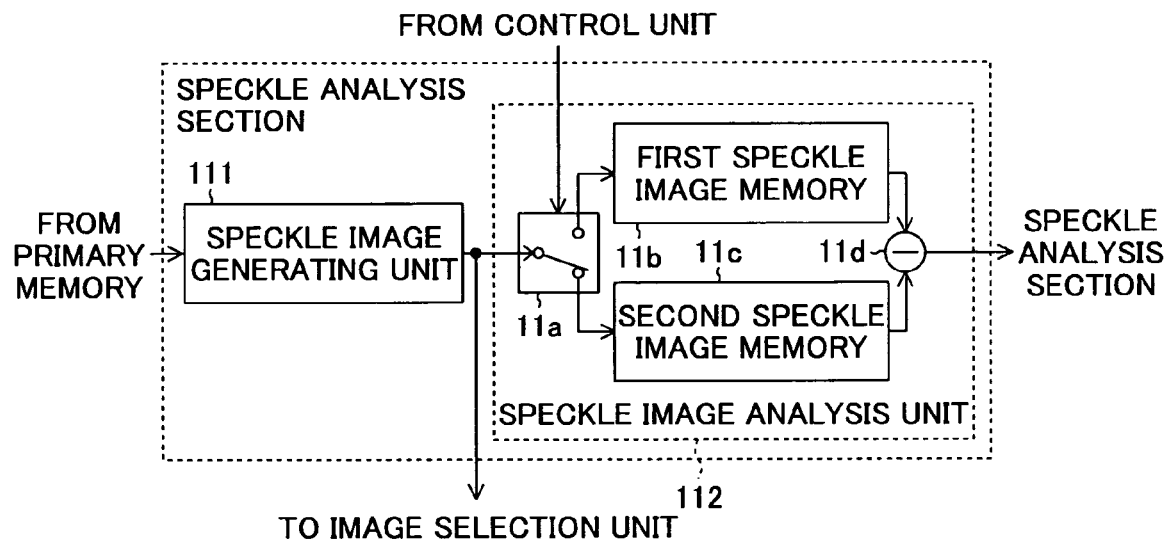
FIG. 2 is a block diagram showing a constitution of a speckle analysis section shown in FIG. 1.

FIG. 2 is a block diagram showing a constitution of the speckle analysis section. As shown in FIG. 2, the speckle image analysis unit 112 includes a switch 11a for alternately switching output destinations of speckle image data, which is outputted from the speckle image generating unit 111, frame by frame, a first speckle image memory 11b for storing speckle image data for one frame outputted from a first output terminal of the switch 11a, a second speckle image memory 11c for storing speckle image data for one frame outputted from a second output terminal of the switch 11a, and a difference calculation part 11d for calculating differences between values of the speckle image data for one frame outputted from the first speckle image memory 11b and values of the speckle image data for one frame outputted from the second speckle image memory 11c to generate speckle analysis result image data representing as a moving image the speckle change between frames, i.e., change of local maximum points and local minimum points of the original data between adjacent two frames.

Referring to FIG. 1 again, under the control of the control unit 102, the image selection unit 113 selects image data to be outputted to the DSC 114 from among the original data outputted from the speckle image generating unit 111 and the speckle analysis result image data outputted from the speckle image analysis unit 112.

The DSC 114 converts the scan format with respect to the data selected by the image selection unit 113 so as to convert image data representing image information in the sound ray direction in the scan space of the ultrasonic beam into image data for display in physical space. That is, the DSC 114 performs resampling in accordance with an image display range by performing coordinate conversion and interpolation according to the scan method of ultrasonic waves. For example, interpolation processing for generating a linear image is performed on the image data obtained by the linear scan. Alternately, polar coordinate conversion and interpolation processing are performed on image data obtained by sector scan, convex scan, or radial scan.

A STC (sensitivity time control) for correcting distance attenuation may be provided in the previous stage of the DSC 114. Further, an image processing unit that performs image processing such as linear gradation processing including gain adjustment and contrast adjustment, or non-linear gradation processing including γ correction, etc. may be provided in the subsequent stage of the DSC 114.

The secondary memory 115 stores image data for display in a format in which raster scan can be performed, for example.

The screen synthesizing unit 116 generates synthesized image data representing an image in which an original image represented by the original data and a speckle analysis result image are superimposed or side-by-side image data representing an image in which the original image and the speckle analysis result image are arranged side-by-side, based on the original data and the speckle analysis result image data generated in the DSC 114 and under the control of the control unit 102. As display formats of images in the synthesized screen, there are a display format in which the original image and the speckle analysis result image are arranged side-by-side in the same size (the first mode side-by-side image), a display format in which they are arranged side-by-side such that the size of the original image is made larger than the size of the speckle analysis result image (the second mode side-by-side image), a display format in which they are arranged side-by-side such that the size of the original image is made smaller than the size of the speckle analysis result image (the third mode side-by-side image), etc. The screen synthesizing unit 116 selects one mode according to a display format selection signal outputted from the control unit 102 and generates the selected one of the first to third mode side-by-side image data. Further, in the case where the display format is not designated by the control unit 102, the screen synthesizing unit 116 performs no synthesizing processing on the original image data and/or speckle analysis result image data and outputs the data without change.

The D/A converter 117 converts image data read from the secondary memory 116 into analog signals and outputs them.

The display unit 118 is a CRT display or an LCD display of a raster scan type, for example, and displays a moving or still image of the ultrasonic image based on the analog converted image signals.

Next, the operation of the ultrasonic imaging apparatus shown in FIG. 1 will be described by referring to FIGS. 1 to 5.

Prior to the start of ultrasonic imaging, the user configures the settings for displaying images in a desired format by using the console 101. For example, in the case where the first mode side-by-side image in which the original image and the speckle analysis result image are arranged side-by-side in the same size on the display unit 118, the user presses down the speckle analysis mode button 10a of the console 101, and then instructs the image selection unit 113 to select the original image and the speckle analysis result image by using the image selection unit control button 10b, and instructs the screen synthesizing unit 116 to generated the first mode side-by-side image by using the screen synthesizing unit control button 10c.

When the user starts ultrasonic imaging, the control unit 102 outputs control signals for starting ultrasonic imaging to the respective units. In response thereto, the drive signal generating unit 105 generates drive signals for driving the respective ultrasonic transducers of the ultrasonic probe 1 in accordance with the scan control unit 104 operating under the control of the control unit 102. Thereby, an ultrasonic beam is transmitted from the ultrasonic transducers, and an object to be inspected is scanned by the scan method such as linear scan, sector scan, convex scan, radial scan, or the like. This ultrasonic beam is reflected by a reflector existing within the object, and plural ultrasonic echoes generated by the reflection are received by the ultrasonic probe 1. The received ultrasonic echoes are converted into electric signals in the respective ultrasonic transducers of the ultrasonic probe 1, and inputted as reception signals to the ultrasonic imaging apparatus main body 2.

The plural reception signals inputted to the ultrasonic imaging apparatus main body 2 are subjected to predetermined signal processing and A/D conversion in the signal processing unit 107, and phase matching and detection processing, and then once stored in the primary memory 110 as original data. When the original data for one frame (frame data) are once stored in the primary memory 110, those original data are outputted to the speckle image generating unit 111 of the speckle analysis section.

Figure 3:
FIG. 3 shows an original image represented by original data.
Figure 4:
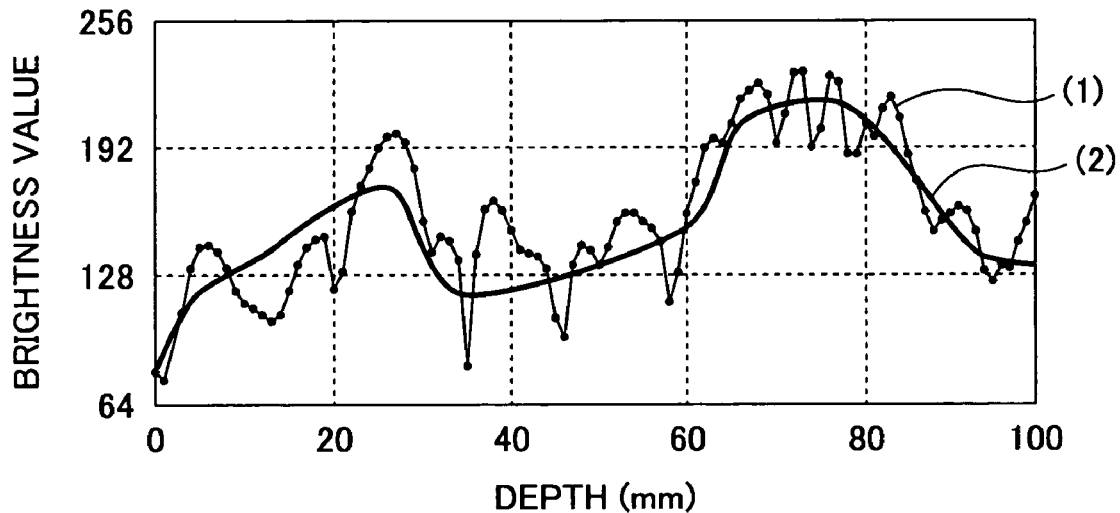
FIG. 4 shows the original data on an area shown by a solid line A-A' in FIG. 3.

FIG. 3 shows an ultrasonic image (original image) represented by the stored original data. Further, a curve (1) shown in FIG. 4 represents original data (brightness values) on an area shown by a dashed line A-A' in FIG. 3, and a curve (2) represents a signal on a structure in the dashed line A-A' in FIG. 3. As shown in FIG. 4, the original data obtained based on the sound ray data includes one signal representing a structure and another signal representing an speckle pattern overlapped each other. Accordingly, as shown in FIG. 3, the structure and the speckle pattern are mixed in the original image.

Figure 5:
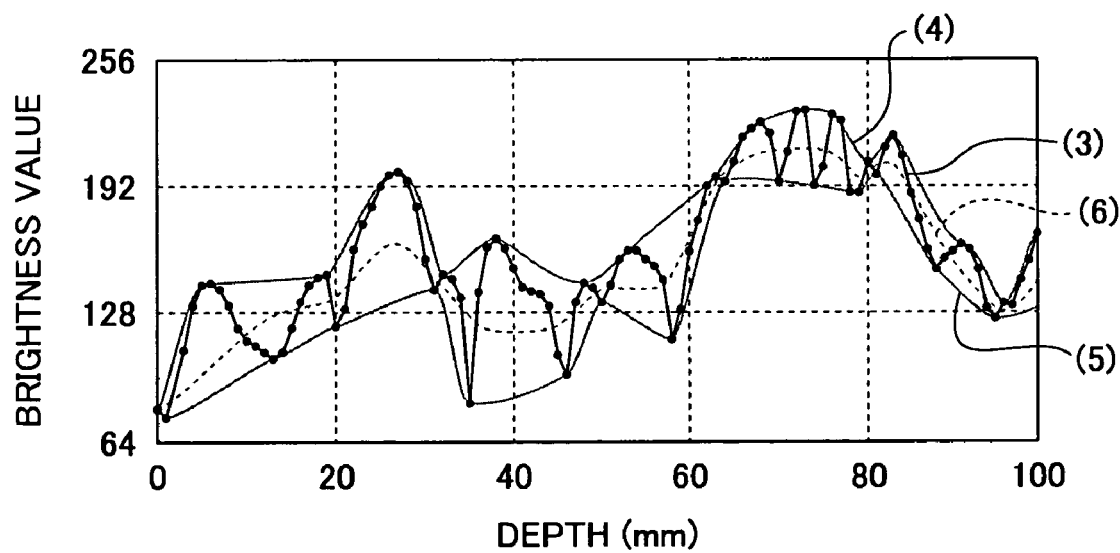
FIG. 5 is a diagram for explanation of a method of extracting structure image data.

Then, the speckle image generating unit 111 extracts structure image data from the original data shown in FIG. 4. For this purpose, at first, the speckle image generating unit 111 obtains a signal representing local maximum points and a signal representing local minimum points in the original data. As shown in FIG. 5, the signal representing local maximum points can be obtained by calculating derivative values at the respective points in the original data shown by the curve (3), obtaining each point, at which the derivative value changes from positive to negative, from those derivative values, and further, performing linear interpolation between those points. Similarly, the signal representing local minimum points can be obtained by obtaining each point, at which the derivative value changes from positive to negative, from derivative values at the respective points in the original data shown by the curve (3), and performing linear interpolation between those points. In FIG. 5, a curve (4) shows a signal representing the local maximum points and a curve (5) shows a signal representing the local minimum points.

Here, if the determination is performed simply based on the derivative values in the original data when local maximum points or local minimum points are extracted, the case might occur where the local maximum/minimum points caused by the speckle and the local maximum/minimum points caused by the structure are mixed. Accordingly, as a determination condition as to whether a certain local maximum point or a certain local minimum point in the original data is employed or not, it is desirable to calculate a distance between one point and the local maximum point or a distance between one point and local minimum point extracted immediately before, and to adopt a condition that the point is not employed if the distance is longer than the wavelength of the transmitted ultrasonic wave.

Then, the speckle image generating unit 111 obtains a signal representing average values of the signal representing the local maximum points and the signal representing the local minimum points. A curve (6) in FIG. 5 shows the signal representing average values. The signal representing average values form the structure image data representing the ultrasonic image of the structure (structure image) in the imaging area. Furthermore, the speckle image generating unit 111 calculates speckle data by subtracting the values represented by the structure image data from the values represented by the original data. At that time, an offset value may be added to the difference values of those according to need. As the offset value, a fixed value that has been set in advance in the ultrasonic imaging apparatus may be used, or a value inputted by a user may be used.

Figure 6A:
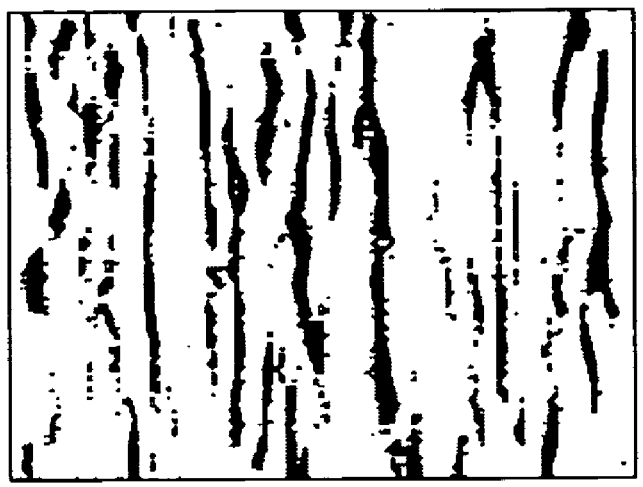
FIGS. 6A and 6B show a speckle image and a structure image separated from the original image, respectively.
Figure 6B:
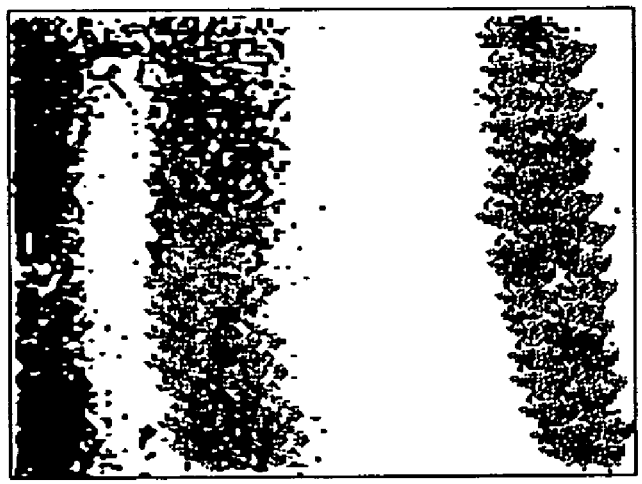

By performing such calculation processing on frame data for one frame, a speckle image shown in FIG. 6A and a structure image shown in FIG. 6B separated from each other can be obtained. Furthermore, by sequentially performing such calculation processing on frame data for plural frames, speckle image data representing a speckle image as a moving image and structure image data representing a structure image as a moving image can be calculated.

Here, in the embodiment, when the signal representing a structure is obtained, not only a general filter processing but the local maximum points and local minimum points in the original data are used for the following reason. That is, the size of the speckle pattern expressed in the imaging area (speckle size) differs depending on the depth of the imaging area. Accordingly, when the filter processing is uniformly performed on the original data, the case occurs where the speckles can not be removed completely, or contrary, the signals representing the structure is removed.

The speckle image generating unit 111 calculates values of mixed data (mixed data value) using the following equation based on the value represented by the generated speckle data (speckle image data value) and the value represented by the structure image data (structure image data value).

Figure 7:
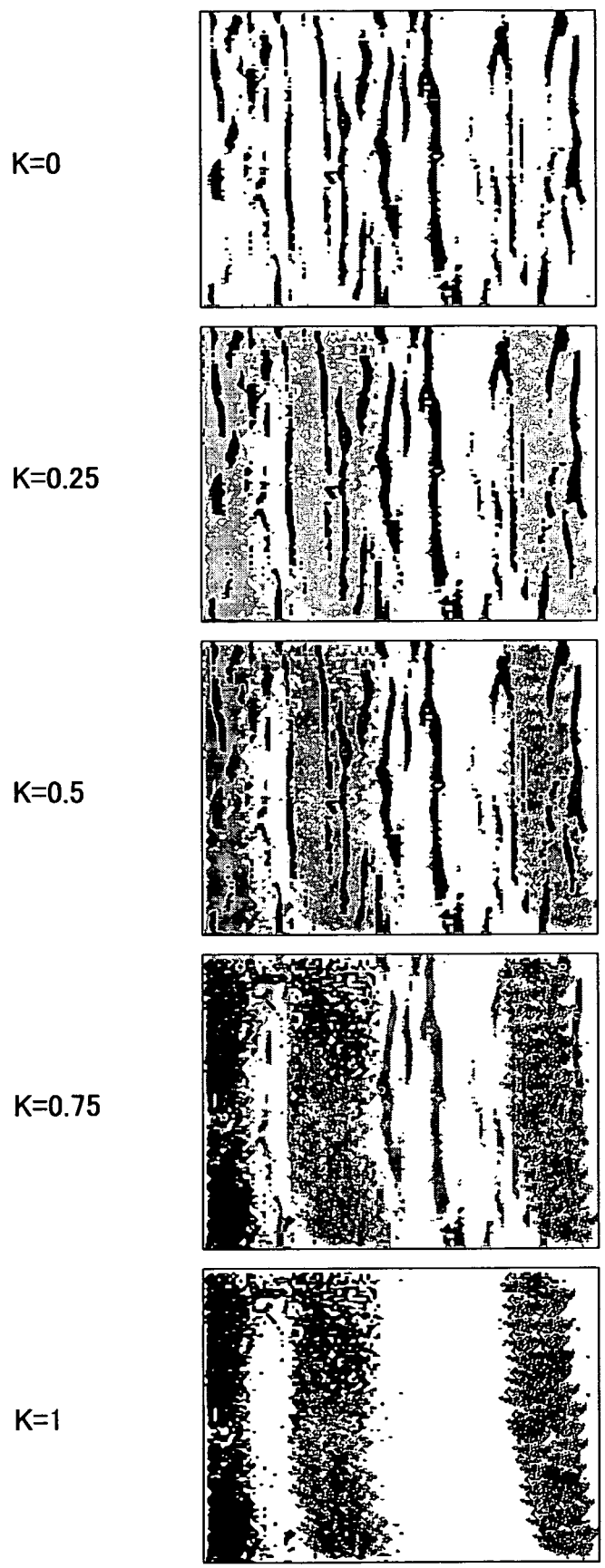
FIG. 7 shows a mixed image of the speckle image and the structure image.

(mixed data value)=(structure image data value)×$K$+
(speckle image data value)×(1−$K$)

Where K represents mixing ratio between the structure image and speckle image, and a desired value within a range $0 \leq K \leq 1$ is inputted by using the console 101 by the user. Thereby, as shown in FIG. 7, the mixed image in which the structure and speckle pattern are mixed at the desired ratio can be obtained. If K=0, the mixed image is an image including only a speckle pattern (i.e., speckle image), and, if K=1, the mixed image is an image including only a structure (i.e., structure image).

The speckle image data representing the speckle image generated by the speckle image generating unit 111 is switched frame by frame by the switch 1a in the speckle image analysis unit 112, and alternately stored in the first speckle image memory 11b and the second speckle image memory 11c. At each time when new speckle image data is stored in the first and second speckle image memories 11b and 11c, the differences between values of the two speckle image data respectively outputted from the first and second speckle image memories 11b and 11c are calculated in the difference calculation part 11d, and thereby, difference image data representing a difference of the speckle images between adjacent two frames is generated as speckle analysis result image data. Thus, the speckle analysis result image data represents change information of local maximum points and local minimum points (change information of speckles) in the original data between adjacent two frames. Furthermore, by sequentially generating such difference image data between frames, speckle analysis result image data representing speckle analysis results as a moving image.

The image selection unit 113 selects, for example, the original data outputted from the primary memory 110 and the speckle analysis result image data (difference image data of speckle images between frames) outputted from the speckle image analysis unit 112 according to the control signal from the control unit 102 for instructing the selection among the original image, the speckle image and the speckle analysis result image, and outputs the selected images to the DSC 114.

The screen synthesizing unit 116 generates, for example, a first mode side-by-side images, in which the original image and the speckle analysis result image are arranged side-by-side in the same size, based on the original data and speckle analysis result image data, which have been scan-converted in the DSC 114, according to the control signal from the control unit 102 for instructing the generation of the first mode side-by-side image.

The image data representing the first mode side-by-side images generated in the screen synthesizing unit 116 is converted into analog signals in the D/A converter 117 and outputted to the display unit 118. Thereby, the first mode side-by-side image, in which the original image and the speckle analysis result image (difference image of the speckle image between frames) are arranged side-by-side in the same size, is displayed on the display unit 118. In this regard, by continuously outputting the original image data and the speckle analysis result image data frame by frame, the first mode side-by-side images, in which the original image and the speckle analysis result image are arranged side-by-side in the same size, can be displayed as a moving image on the display unit 118.

As described above, according to the embodiment, the difference image between frames of speckle images can be generated and displayed as a moving image on the display unit 118. Further, the synthesized image, in which the original image and the speckle analysis result image are synthesized with each other, or the side-by-side images, in which the original images and the speckle analysis result images are arranged side-by-side, can be displayed on the display unit 118 according to a choice of the user. Therefore, an appropriate moving image is displayed on the screen according to diagnostic purposes, and thereby, the diagnoses by doctors are facilitated and the quality of diagnoses can be improved.

Next, an ultrasonic imaging apparatus according to the second embodiment of the present invention will be described.

Figure 8:
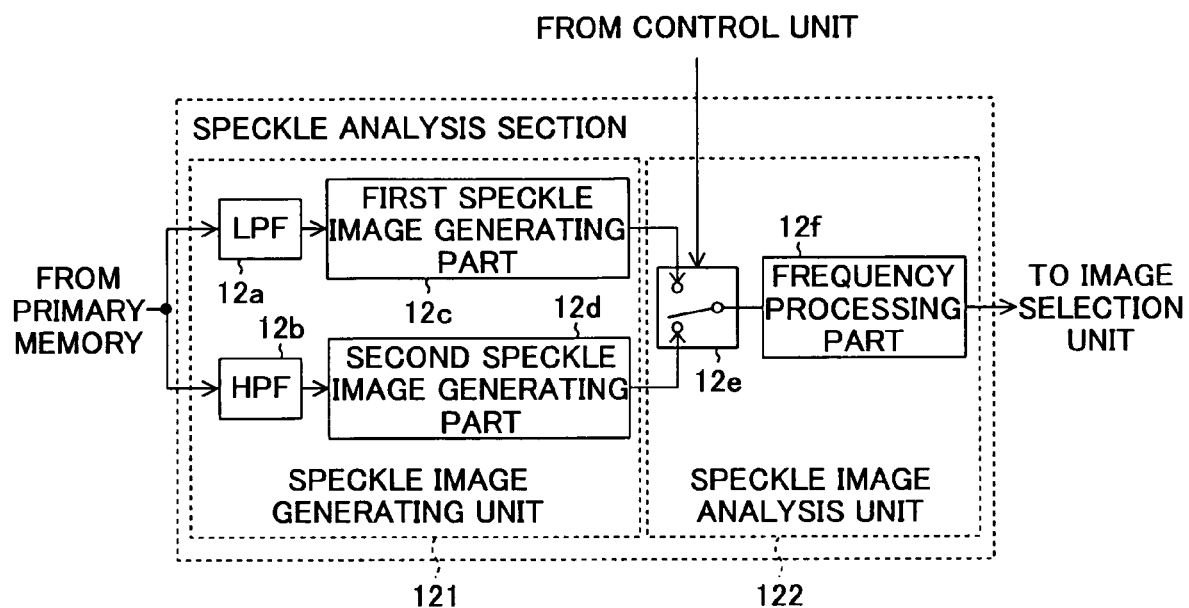
FIG. 8 is a block diagram showing a constitution of a speckle analysis section included in an ultrasonic imaging apparatus according to the second embodiment of the present invention.

FIG. 8 is a block diagram showing part of the ultrasonic imaging apparatus according to the embodiment. As shown in FIG. 8, the ultrasonic imaging apparatus according to the embodiment includes a speckle image generating unit 121 and a speckle image analysis unit 122 as a speckle analysis section. Other constitution and operation are the same as those in the ultrasonic imaging apparatus shown in FIG. 1.

The speckle image generating unit 121 includes a LPF (low-pass filter) 12a for extracting low frequency components of an image signal represented by the original data outputted from the first memory 110, a first speckle image generating part 12c for generating first speckle image data based on the low frequency components extracted by the LPF 12a, a HPF (high-pass filter) 12b for extracting high frequency components of an image signal represented by the original data outputted from the first memory 110, and a second speckle image generating part 12d for generating second speckle image data based on the high frequency components extracted by the HPF 12b.

Figure 9:
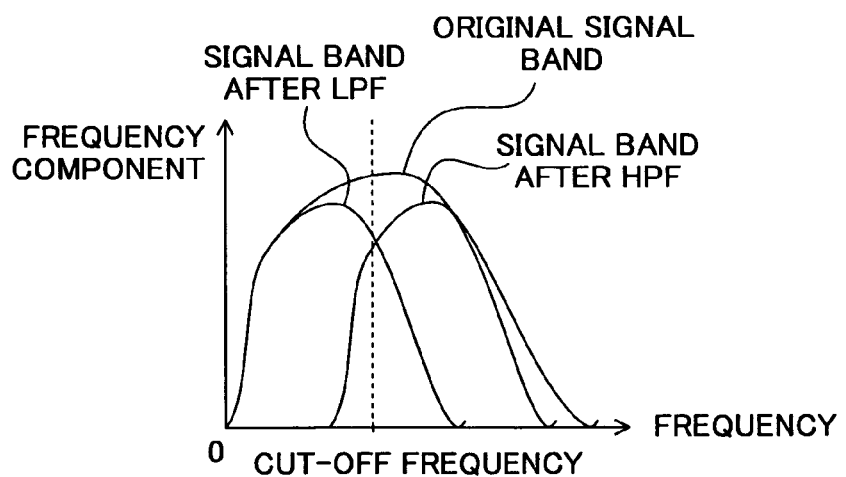
FIG. 9 is a diagram for explanation of frequency characteristics of a LPF and a HPF shown in FIG. 8.

Here, the LPF 12a and HPF 12b have frequency characteristics as shown in FIG. 9. That is, with respect to a substantially center frequency of an original signal band (the frequency range of the image signal represented by the original data) as a cut-off frequency, the LPF 12a extracts only the lower frequency range from the original signal band, and the HPF 12b extracts only the higher frequency range from the original signal band.

Further, the speckle image analysis unit 122 includes a switch 12e for selecting one of the speckle image data outputted from the first speckle image generating part 12c and the speckle image data outputted from the second speckle image generating part 12d to output the selected data from an output terminal under the control of the control unit 102, and a frequency processing part 12f for generating image data representing depth-dependent change of low frequency component intensity or high frequency component intensity contained in a speckle image for one frame by performing the following processing on the speckle image data for one frame inputted via the switch 12e.

Figure 10A:
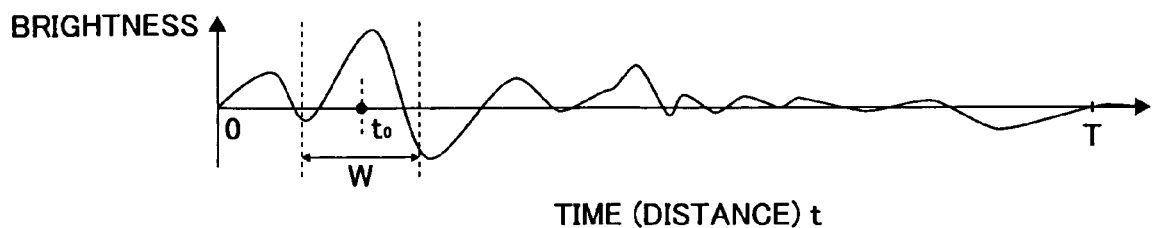
FIGS. 10A-10C are diagrams for explanation of frequency processing in a frequency processing part.
Figure 10B:
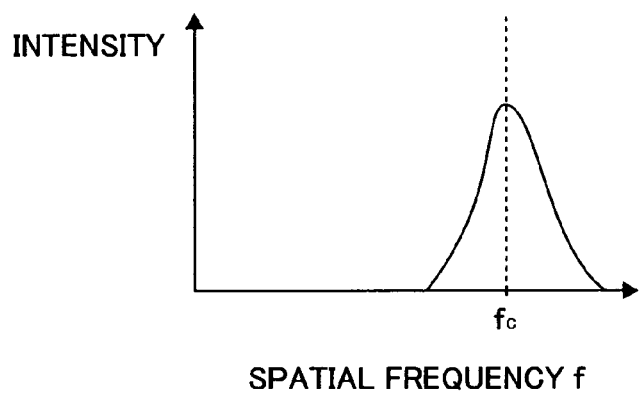
Figure 10C:
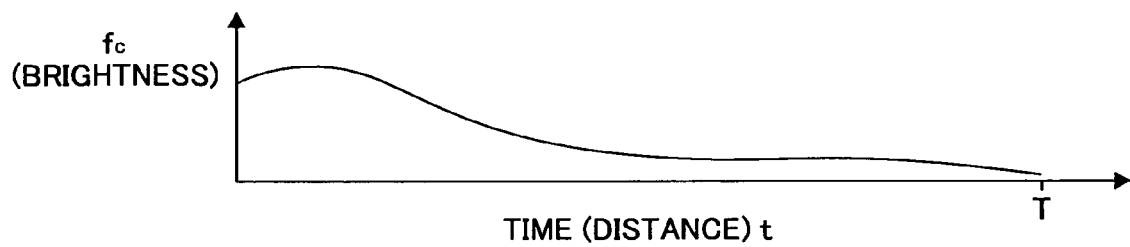

FIGS. 10A-10C are diagrams for explanation of the frequency processing performed on ultrasonic image data (speckle image data) in the frequency processing part 12f. FIG. 10A shows a signal representing a brightness value corresponding one line in the depth direction of the ultrasonic image data (speckle image data). In FIG. 10A, the horizontal axis indicates time "t", and this corresponds to a distance in the depth direction of the object. Further, FIG. 10B represents a spatial frequency distribution of the signal shown in FIG. 10A, and the horizontal axis indicates spatial frequency "f", and the vertical axis indicates signal intensity. Furthermore, FIG. 10C shows an analysis result of the signal shown in FIG. 10A, and the horizontal axis indicates time "t" and the vertical axis indicates brightness value.

As shown in FIG. 10A, at first, the frequency processing part 12f extracts a signal with respect to each line from the ultrasonic image data for one frame, and performs waveform/frequency transform processing with respect to a time period having a window width W around time $t_0$ with respect to a signal for one line. As the waveform/frequency transform processing, a known conversion processing such as fast Fourier transform (FFT) or wavelet transform may be used. In the embodiment, FFT is used. As a result, the spatial frequency distribution as shown in FIG. 10B is obtained. The center frequency or peak frequency $f_c$ of the spatial frequency distribution is used as a representative value (feature quantity) at time "t".

The frequency processing part 12f also performs such processing on other time periods within a range $W/2 < t_0 < T - W/2$ by shifting time $t_0$. Here, T represents a time period for one line. A time interval Δt, by which the time $t_0$ is shifted, is made equal to a time interval between sampling points on one line or larger than the time interval. Further, the relationship between the time interval Δt and the window width W is desirably set to $0 < \Delta t \leq W$ such that there is no gap in a range to be analyzed. Furthermore, the window width W, the lower limit W/2 of the time $t_0$ and the upper limit (T−W/2) of the time $t_0$ may be varied as long as they satisfy the above condition. Thereby, as shown in FIG. 10C, the analysis result of the ultrasonic image for one line is obtained. By converting the intensity at the center frequency or peak frequency $f_c$ in the analysis result into a brightness value, analysis data of the ultrasonic image is obtained.

Further, by obtaining the representative values where $0 < t_0 < T$ by performing the same frequency processing with respect to all lines of the ultrasonic image, analysis data of the ultrasonic image for one frame is obtained. The image represented by performing DSC processing on the analysis data represents depth-dependent change of the spatial frequency components contained in the ultrasonic image.

The frequency processing part 12f shown in FIG. 8 performs such processing on the speckle images in the low frequency range or the speckle images in the high frequency range generated by the speckle image generating unit 121. Thereby, low frequency component intensity image data or high frequency component intensity image data representing depth-dependent change of the low frequency component intensity or high frequency component intensity contained in the speckle image for one frame is obtained. The image data is used as speckle analysis result image data.

Next, an ultrasonic imaging apparatus according to the third embodiment of the present invention will be described.

Figure 11:
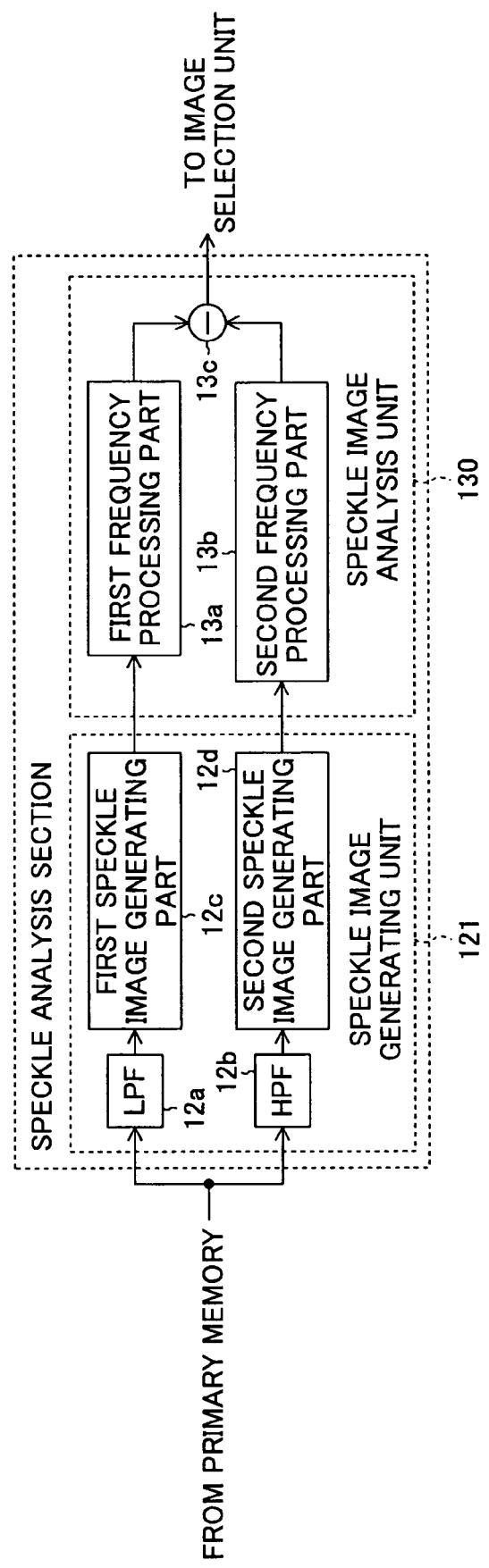
FIG. 11 is a block diagram showing a constitution of a speckle analysis section included in an ultrasonic imaging apparatus according to the third embodiment of the present invention.

FIG. 11 is a block diagram showing a part of the ultrasonic imaging apparatus according to the embodiment. As shown in FIG. 11, the ultrasonic imaging apparatus according to the embodiment includes a speckle image generating unit 121 and a speckle image analysis unit 130 as a speckle analysis section. The constitution and operation of the speckle image generating unit 121 are the same as those described in the second embodiment. Other constitution and operation are the same as those in the ultrasonic imaging apparatus shown in FIG. 1.

The speckle image analysis unit 130 generates speckle image analysis data representing depth-dependent change of a difference between low frequency component intensity and high frequency component intensity contained in a speckle image for one frame. The speckle image analysis unit 130 includes a first frequency processing part 13a, a second frequency processing part 13b and a difference calculation part 13c.

The first frequency processing part 13a performs the frequency processing that has been described by referring to FIGS. 10A-10C on the first speckle image data outputted from the first speckle image generating part 12c to generate low frequency component intensity image data representing depth-dependent change of intensity of low frequency component contained in the first speckle image.

The second frequency processing part 13b performs the frequency processing that has been described by referring to FIGS. 10A-10C on the second speckle image data outputted from the second speckle image generating part 12d to generate high frequency component intensity image data representing depth-dependent change of intensity of high frequency component contained in the second speckle image.

The difference calculation part 13c calculates differences between values of the low frequency component intensity image data outputted from the first frequency processing part 13a and values of the high frequency component intensity image data outputted from the second frequency processing part 13b to generate speckle analysis result image data representing depth-dependent change of a difference between the low frequency component intensity in the first speckle image and the high frequency component intensity in the second speckle image, as a moving image.

Next, an ultrasonic imaging apparatus according to the fourth embodiment of the present invention will be described.

Figure 12:
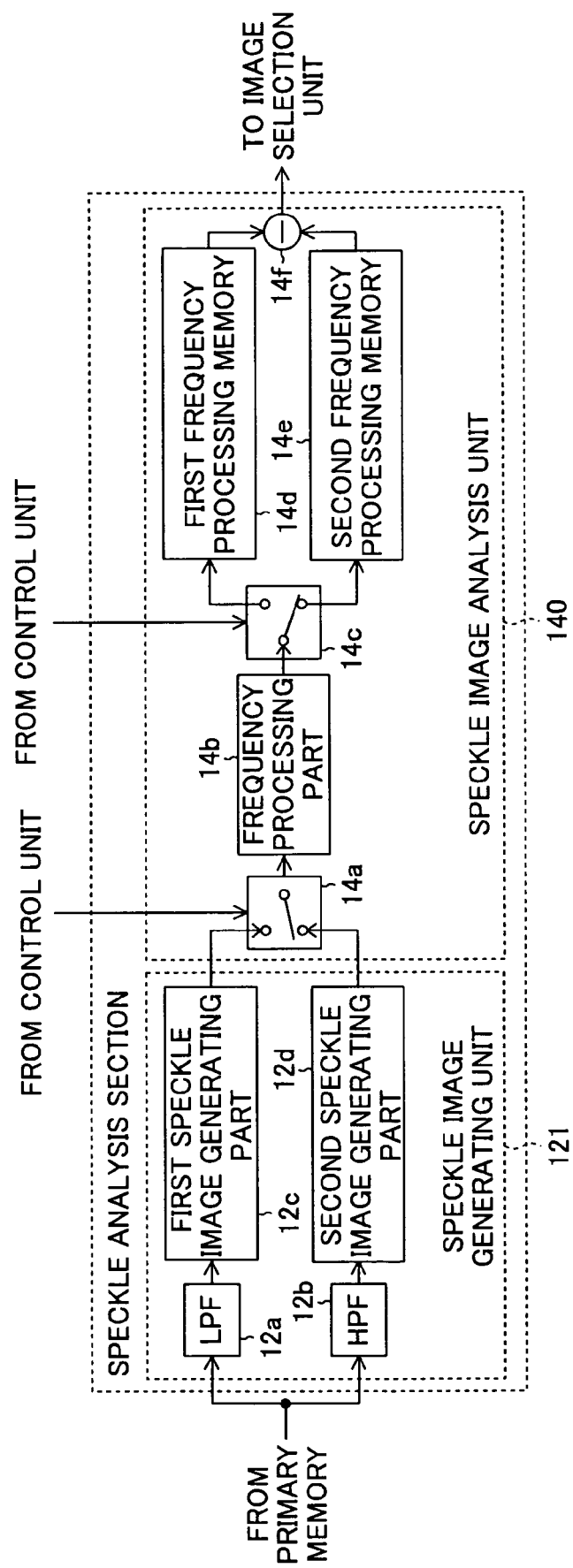
FIG. 12 is a block diagram showing a constitution of a speckle analysis section included in an ultrasonic imaging apparatus according to the fourth embodiment of the present invention.

FIG. 12 is a block diagram showing part of the ultrasonic imaging apparatus according to the embodiment. As shown in FIG. 12, the ultrasonic imaging apparatus according to the embodiment includes a speckle image generating unit 121 and a speckle image analysis unit 140 as a speckle analysis section. The constitution and operation of the speckle image generating unit 121 are the same as those described in the second embodiment. Other constitution and operation are the same as those in the ultrasonic imaging apparatus shown in FIG. 1.

The speckle image analysis unit 140 generates speckle image analysis data representing change between frames in the low frequency component intensity or high frequency component intensity in the speckle image. The speckle image analysis unit 140 includes a first switch 14a, a frequency processing part 14b, a second switch 14c, a first frequency processing memory 14d, a second frequency processing memory 14e and a difference calculation part 14f.

The first switch 14a selects one of speckle image data output from the first and second speckle image generating parts 12c and 12d and outputs the selected image data from an output terminal under the control of the control unit 102.

The frequency processing part 14b by performs the frequency processing that has been described by referring to FIGS. 10A-10C on the first or second speckle image data outputted from the first switch 14a to generate low frequency component intensity image data representing depth-dependent change of low frequency component intensity in the first speckle image or high frequency component intensity image data representing depth-dependent change of high frequency component intensity in the second speckle image.

The second switch 14c switches the low frequency component intensity image data or high frequency component intensity image data, which is outputted from the frequency processing part 14b, frame by frame and alternately outputs the image data from the first and second output terminals alternately under the control of the control unit 102.

The first frequency processing memory 14d stores the low frequency component intensity image data or high frequency component intensity image data outputted from the first output terminal of the second switch 14c. The second frequency processing memory 14e stores the low frequency component intensity image data or high frequency component intensity image data outputted from the second output terminal of the second switch 14c.

The difference calculation part 14f generates differences between values of the low frequency component intensity image data or high frequency component intensity image data read out from the first frequency processing part 14d and values of the low frequency component intensity image data or high frequency component intensity image data read out from the second frequency processing part 14e. Thereby, speckle analysis result image data representing change between frames in the depth-dependent change of low frequency component intensity in the first speckle image or the depth-dependent change of high frequency component intensity in the second speckle image, as a moving image. Thus, a moving target can be captured.

Next, an ultrasonic imaging apparatus according to the fifth embodiment of the present invention will be described.

Figure 13:
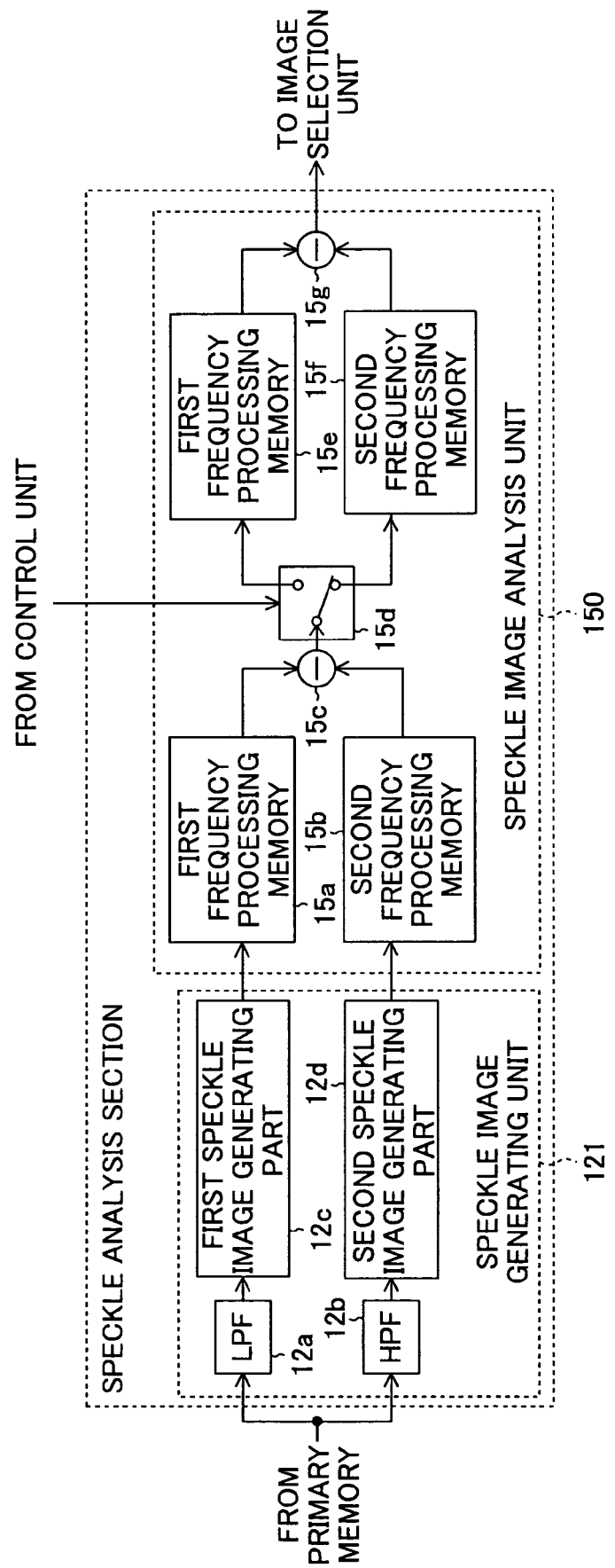
FIG. 13 is a block diagram showing a constitution of a speckle analysis section included in an ultrasonic imaging apparatus according to the fifth embodiment of the present invention.

FIG. 13 is a block diagram showing apart of the ultrasonic imaging apparatus according to the embodiment. As shown in FIG. 13, the ultrasonic imaging apparatus according to the embodiment includes a speckle image generating unit 121 and a speckle image analysis unit 150 as a speckle analysis section. The constitution and operation of the speckle image generating unit 121 are the same as those described in the second embodiment. Other constitution and operation are the same as those in the ultrasonic imaging apparatus shown in FIG. 1.

The speckle image analysis unit 150 generates speckle image analysis data representing change between frames in the low frequency component intensity in the first speckle image or high frequency component intensity in the second speckle image. The speckle image analysis unit 150 includes a first frequency processing part 15a, a second frequency processing part 15b, a first difference calculation part 15c, a switch 15d, a first frequency processing memory 15e, a second frequency processing memory 15f and a second difference calculation part 15g.

The first frequency processing part 15a performs the frequency processing that has been described by referring to FIGS. 10A-10C on the first speckle image data outputted from the first speckle image generating part 12c to generate low frequency component intensity image data representing depth-dependent change of low frequency component intensity in the first speckle image.

The second frequency processing part 15b performs the frequency processing that has been described by referring to FIGS. 10A-10C on the second speckle image data outputted from the second speckle image generating part 12d to generate high frequency component intensity image data representing depth-dependent change of high frequency component intensity in the second speckle image.

The first difference calculation part 15c calculates differences between values of the low frequency component intensity image data outputted from the first frequency processing part 15a and values of the high frequency component intensity image data outputted from the second frequency processing part 15b to generate low and high frequency component intensity difference image data representing depth-dependent change of a difference between the low frequency component intensity in the first speckle image and the high frequency component intensity in the second speckle image.

The first switch 15d switches the low and high frequency component intensity difference image data outputted from the first difference calculation part 15c frame by frame to output the image data from the first and second output terminals alternately under the control of the control unit 102.

The first frequency processing memory 15e stores the low and high frequency component intensity difference image data outputted from the first output terminal of the first switch 15d. The second frequency processing memory 15f stores the low and high frequency component intensity difference image data outputted from the second output terminal of the first switch 15d.

The second difference calculation part 15g calculates differences between values of the low and high frequency component intensity image data read out from the first frequency processing memory 15e and values of the low and high frequency component intensity image data read out from the second frequency processing memory 15f. Thereby, speckle analysis result image data representing the change between frames in the depth-dependent change of a difference between the low frequency component intensity in the first speckle image and the high frequency component intensity in the second speckle image, as a moving image.

In the above description, the switch 11a as shown in FIG. 2, the second switch 14c as shown in FIG. 12, and the switch 15d as shown in FIG. 13 have been operated under the control of the control unit 102, however, they may be operated under the control of the scan control unit 104.

Further, the speckle analysis section as shown in FIGS. 8, 11, 12 and 13 performs frequency processing of the original signal by separating the original signal band into the low frequency range and the high frequency range, however, the frequency processing may be performed by separating the original signal band into three or more frequency ranges (e.g., three of a low frequency range, a middle frequency range and a high frequency range).

Furthermore, the speckle image generating unit 111 as shown in FIG. 1, and the first and second speckle image generating parts 12c and 12d as shown in FIGS. 8 and 11-13 may generate speckle images by using the following two-dimensional mask processing.

Figure 14:
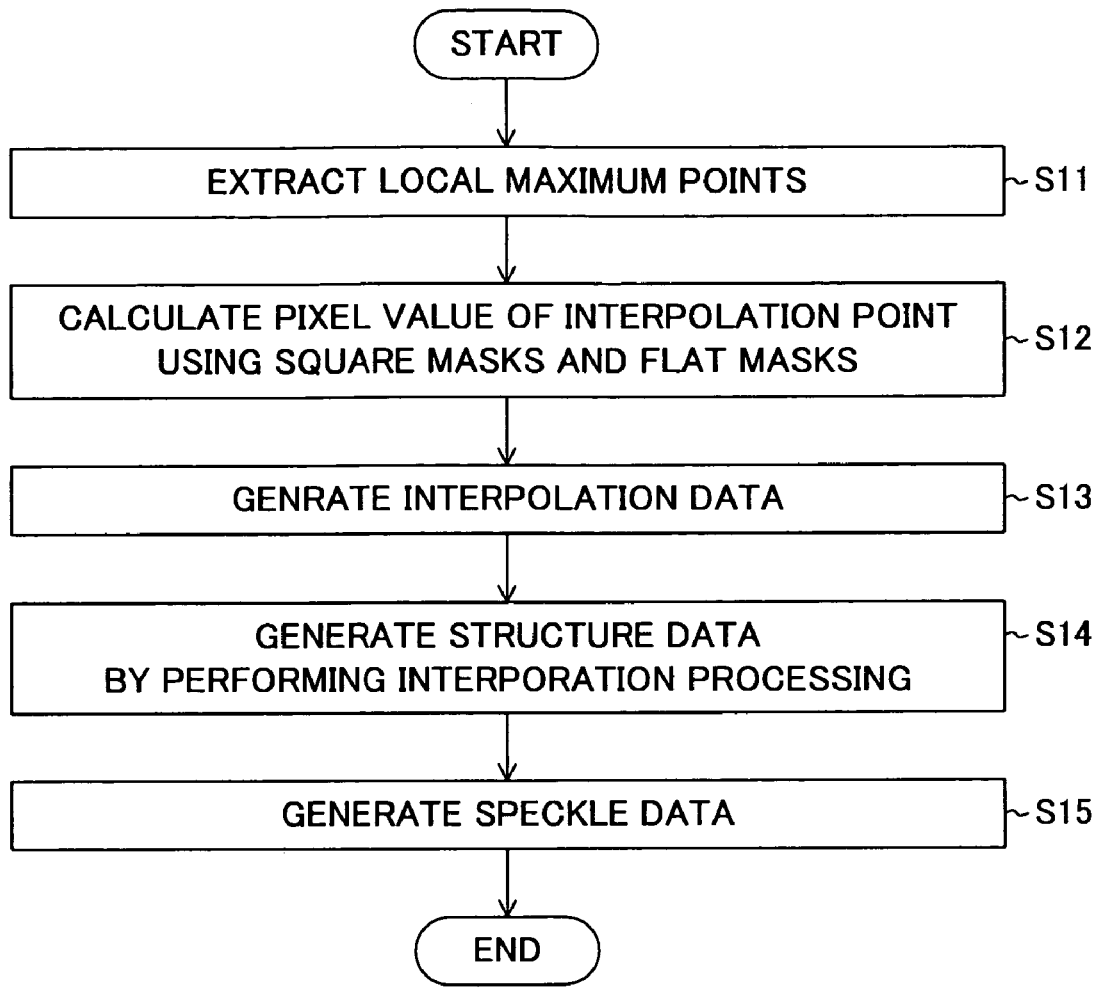
FIG. 14 is a flowchart showing an ultrasonic image processing method.

FIG. 14 is a flowchart showing a speckle image generating method of generating speckle images by using two-dimensional mask processing. This speckle image generating method is performed on the original data obtained by performing linear scan and characterized by use of two-dimensional mask processing in this regard.

Figure 15:
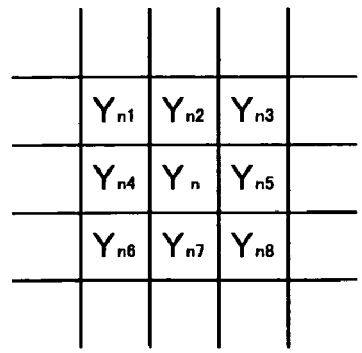
FIG. 15 is a diagram for explanation of a method of extracting local maximum points of pixels.

At step S11 in FIG. 14, local maximum points in the original image are extracted based on the original data. The local maximum points can be extracted by the following method, for example. As shown in FIG. 15, attention is focused on a certain pixel $Y_n$, and the pixel value (brightness value) $D(Y_n)$ of the pixel $Y_n$ and pixel values $(Y_{n1})$ to $D(Y_{n8})$ of pixels $Y_1$ to $Y_8$ located in the periphery thereof are compared. Then, if the pixel value $D(Y_n)$ is larger than the pixel values of the surrounding pixels, that is, all of the relational expressions $D(Y_n)>(Y_{n1})$, $D(Y_n)>(Y_{n2})$, $D(Y_n)>(Y_{n3})$, $D(Y_n)>(Y_{n4})$, $D(Y_n)>(Y_{n5})$, $D(Y_n)>(Y_{n6})$, $D(Y_n)>(Y_{n7})$, and $D(Y_n)>(Y_{n8})$ are satisfied, $Y_n$ is judged as a local maximum point.

Then, at step S12 in FIG. 14, a pixel value of an interpolation point is calculated by four-point interpolation using square interpolation masks or flat interpolation masks in order to interpolate the extracted local maximum points.

FIGS. 16A and 16B are diagrams for explanation of a method of performing four-point interpolation by using square interpolation masks, and shaded areas show local maximum points extracted at step S11. As shown in FIG. 16A, in order to obtain four points to be used for calculating the pixel value of the interpolation point Y, first, with the interpolation point Y as a center, surrounding pixels are divided into four quadrants. Then, by using the square interpolation masks $M_1, M_2 \ldots$ as shown in FIG. 16B sequentially in ascending order of mask size, the local maximum points near the interpolation point Y are explored in the first quadrant to the fourth quadrant, respectively. The pixels $Y_1$ to $Y_4$ as shown in FIG. 16A show the local maximum points respectively explored in the first quadrant to the fourth quadrant.

Then, the pixel value $D(Y)$ of the interpolation point Y is calculated based on the positions of the explored pixels $Y_1$ to $Y_4$ and the pixel values $D(Y_1)$ to $D(Y_4)$. For this purpose, the pixel value $D(Y_A)$ at a point $Y_A$ on one axis including the pixel Y is calculated by the weighed average method by using the pixel value $D(Y_1)$ of the pixel $Y_1$ and the pixel value $D(Y_2)$ of the pixel $Y_2$, and the pixel value $D(Y_B)$ at a point $Y_B$ on one axis including the pixel Y is calculated by using the pixel value $D(Y_3)$ of the pixel $Y_3$ and the pixel value $D(Y_4)$ of the pixel $Y_4$. Further, the pixel value $D(Y)$ of the interpolation point Y is calculated by the weighed average method by using the positions of the points $Y_A$ and $Y_B$ and the pixel values $D(Y_A)$ and $D(Y_B)$.

FIGS. 17A and 17B are diagrams for explanation of a method of performing four-point interpolation by using flat interpolation masks. In this embodiment, non-square masks extending in the vertical direction in the drawing (i.e., depth direction in the object) are used. As shown in FIG. 17A, in order to obtain four points to be used for calculating the pixel value of the interpolation point Y, at first, with the interpolation point Y as a center, surrounding pixels are divided into four quadrants. Then, by using the flat interpolation masks $M_1', M_2' \ldots$ as shown in FIG. 17B sequentially in ascending order of mask size, the local maximum points near the interpolation point Y are explored in the first quadrant to the fourth quadrant, respectively. In FIG. 17A, the pixels $Y_5$ to $Y_8$ show the local maximum points respectively in the first quadrant to the fourth quadrant.

Then, the pixel value $D(Y)'$ of the interpolation point Y is calculated based on the positions of the explored pixels $Y_5$ to $Y_8$ of the explored local maximum points and the pixel values $D(Y_5)$ to $D(Y_8)$. The method of calculating the pixel value $D(Y)'$ is the same as that for the square interpolation masks.

Referring to FIG. 14 again, at step S13, interpolation data is generated based on the pixel value $D(Y)$ calculated by using the square interpolation masks and the pixel value $D(Y)'$ calculated by using the flat interpolation masks.

Here, the image interpolation processed by using the square interpolation masks is good in continuousness in lateral lines, however, not very good in continuousness in diagonal lines. On the other hand, the image interpolation processed by using the flat interpolation masks is good in continuousness in diagonal lines, however, not very good in continuousness in lateral lines. Accordingly, in the embodiment, the interpolation data is generated by comparing the pixel value D(Y) calculated by using the square interpolation masks and the pixel value D(Y)' calculated by using the flat interpolation masks, and adopting the value of the larger pixel value as the pixel value in the interpolation point Y.

Then, at step S14, by using the interpolation data generated at step S13, interpolation processing is performed with respect to data at local maximum points extracted at step S11. Thus generated image data forms structure image data representing an ultrasonic image of the structure (structure image) in the imaging region.

Then, at step S15, the speckle image data representing the speckle image is generated by subtracting the values represented by the structure image data generated at step S14 from the values represented by the original data.

According to the speckle image generating method, since the interpolation processing is performed based on the pixel values obtained by using the square interpolation masks and the flat interpolation masks, the structure image good in continuousness in lateral lines and diagonal lines can be obtained. Therefore, by using such a structure image, a speckle image good in separation from the structure can be obtained.

As a modified example of the speckle image processing method according to the embodiment, interpolation data may be generated by using one of the square interpolation masks and the flat interpolation masks at steps S12 and S13 as shown in FIG. 14. In the case of using the square interpolation masks, a structure image good in continuousness in lateral lines can be acquired, and, in the case of using the flat interpolation masks, a structure image good in continuousness in diagonal lines can be acquired. Alternatively, when the interpolation data is generated at step S13, it may be selected to use the pixel values obtained by using the square interpolation masks, the pixel values obtained by using the flat interpolation masks, or the pixel values selected by comparing those pixel values. Thereby, a structure image desired by the user can be acquired.

Furthermore, the speckle image generating unit 111 as shown in FIG. 1, and the first and second speckle image generating parts 12c and 12d as shown in FIGS. 8 and 11-13 may generate speckle images by using the following two-dimensional mask processing.

Figure 18:
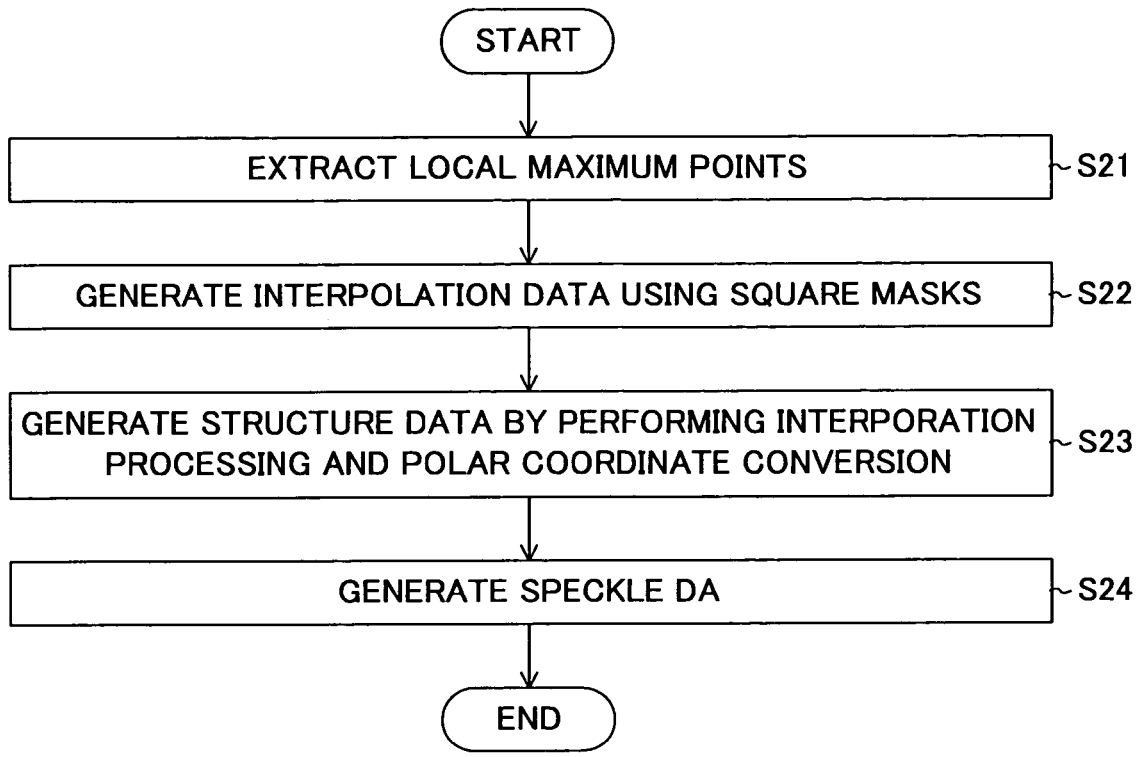
FIG. 18 is a flowchart showing another ultrasonic image processing method.

FIG. 18 is a flowchart showing another speckle image generating method of generating speckle images by using two-dimensional mask processing. The speckle image generating method is performed on the original data obtained by performing sector scan, convex scan or radial scan and characterized by use of two-dimensional mask processing in this regard.

At step S21 shown in FIG. 18, local maximum points in the original image are extracted based on the original data. Then, at step S22, interpolation data is generated by calculating the pixel value of the interpolation point for interpolation of local maximum points by four-point interpolation by using square interpolation masks. Note that the extraction processing of the local maximum points at step S21 and the calculation processing of the pixel value at S22 are the same as described at steps S11 and S12 in FIG. 14 by referring to FIGS. 15-16B.

Then, at step S23, interpolation processing is performed with respect to data at local maximum points extracted at step S21 by using the interpolation data generated at step S22, and further, polar coordinate conversion processing (scan conversion processing) in accordance with the scan method of ultrasonic wave is performed. Thereby, image data representing a sector image, convex image or radial image is generated. Such image data forms structure image data representing structure image in the imaging region.

Then, at step S24, the speckle data representing the speckle image is generated by subtracting the values represented by the structure image data from the values represented by the original data.

According to the speckle image generating method, since the interpolation processing and the polar coordinate conversion processing are performed based on the pixel value calculated by using the square interpolation masks good in continuousness in lateral lines, a structure image good in continuousness can be obtained. Therefore, by using such a structure image, a speckle image good in separation from the structure can be obtained.

Figure 19:
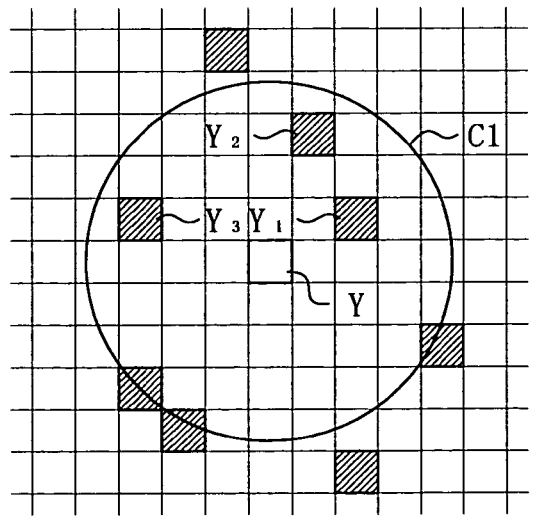
FIG. 19 is a diagram for explanation of another method of calculating a pixel value of an interpolation point.

In the above-mentioned two speckle image generating methods, the pixel value of the interpolation point is calculated by performing the four-point interpolation by using local maximum points, however, the pixel value may be calculated by using other methods. For example, as shown in FIG. 19, pixel values of the local maximum points $Y_1$, $Y_2$, $Y_3$ . . . included within a predetermined range from the interpolation point Y (e.g., inside of a circle C1 around the interpolation point Y). In this case, the pixel value D(Y) of the interpolation point Y can be calculated by the following equation. In the equation (1), $d_1$, $d_2$ and $d_3$ represent the distances between the interpolation point Y and the local maximum points $Y_1$, $Y_2$ and $Y_3$, respectively.

$$D(Y) = (1/d_1)(1/d_1 + 1/d_2 + 1/d_3) \times Y_1 + \quad (1)$$
$$(1/d_2)(1/d_1 + 1/d_2 + 1/d_3) \times Y_2 +$$
$$(1/d_3)(1/d_1 + 1/d_2 + 1/d_3) \times Y_3$$

According to the method, the time for exploring the pixels of the local maximum points to be used when the pixel value of the pixel Y is calculated can be shortened.

Alternatively, in place of the equation (1), the pixel value of the pixel Y may be calculated using the following equation (2) or (3).

$$D(Y) = (1/d_1^2)(1/d_1^2 + 1/d_2^2 + 1/d_3^2) \times Y_1 + \quad (2)$$
$$(1/d_2^2)(1/d_1^2 + 1/d_2^2 + 1/d_3^2) \times Y_2 +$$
$$(1/d_3^2)(1/d_1^2 + 1/d_2^2 + 1/d_3^2) \times Y_3$$

$$D(Y) = (1/d_1^3)(1/d_1^3 + 1/d_2^3 + 1/d_3^3) \times Y_1 + \quad (3)$$
$$(1/d_2^3)(1/d_1^3 + 1/d_2^3 + 1/d_3^3) \times Y_2 +$$
$$(1/d_3^3)(1/d_1^3 + 1/d_2^3 + 1/d_3^3) \times Y_3$$

In the case of using the equation (2) or (3), the local maximum points near the pixel Y exert a larger influence compared to the case of using the equation (1).

Further, in the above-mentioned two speckle image generating methods, the structure image data is generated using the local maximum points in the original image, however, in place of the local maximum points, local minimum points or average points of the local maximum points and the local minimum points may be used.

Furthermore, the speckle image generating unit 111 shown in FIG. 1, and the first and second speckle image generating parts 12c and 12d shown in FIGS. 8 and 11-13 may perform the following frequency range division processing on the speckle image data and the structure image data. The frequency range division processing refers to image processing of dividing an ultrasonic image into plural frequency ranges and enhancing a desired frequency component.

Figure 20:
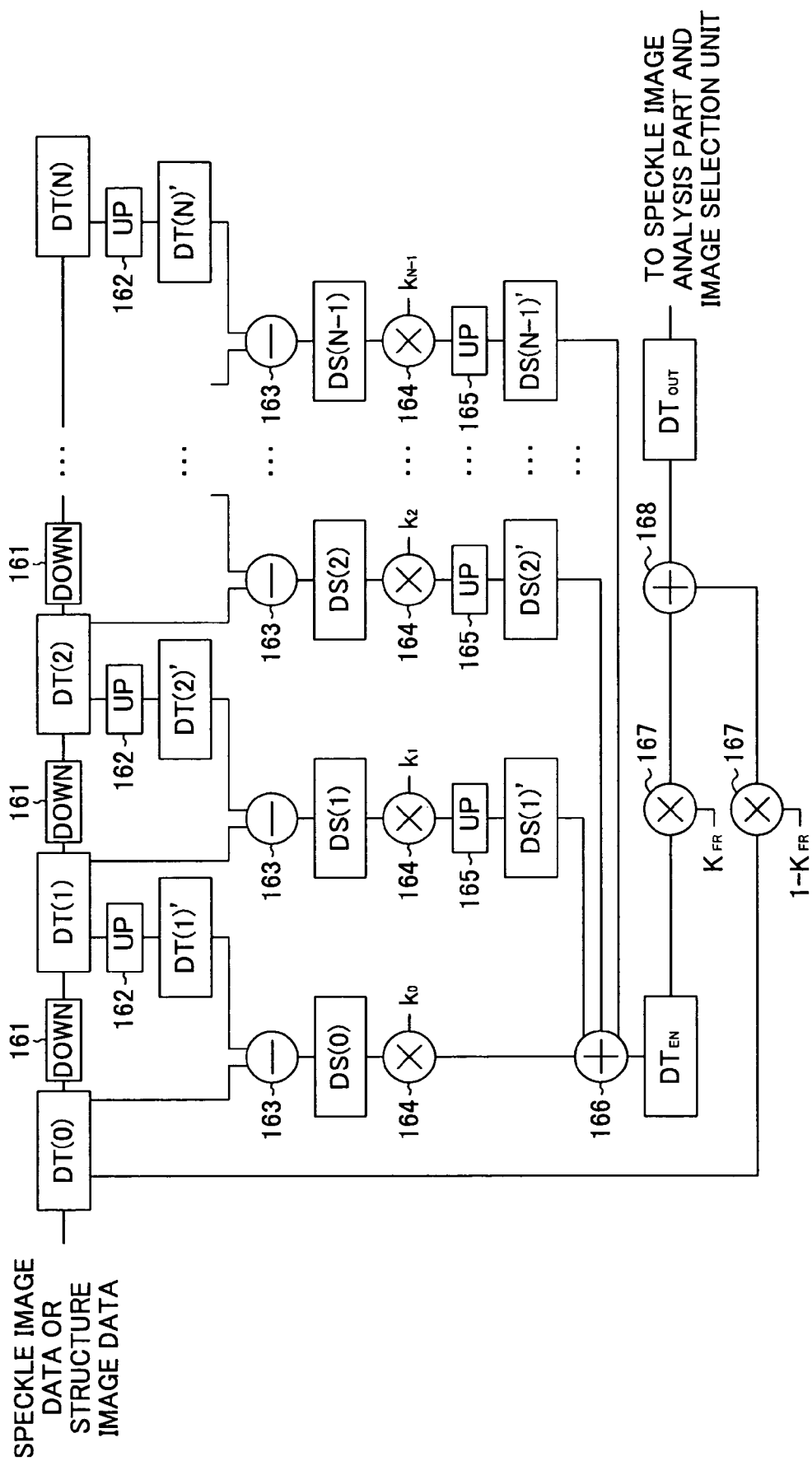
FIG. 20 is a diagram for explanation of frequency range division processing.

As shown in FIG. 20, when speckle image data or structure image data (hereinafter, referred to as "image data DT(0)") generated in the speckle image generating unit 1a is thinned out in a down-sampling unit 161, and filter processing such as Nyquist filter processing is performed on the thinned out data. By repeating such processing, down-sampling data DT(1), DT(2), . . . , DT(N) having low spatial frequency components are sequentially generated.

Then, in an up-sampling unit 162, value "0" data is inserted into the (n)th down-sampling data DT(n) (n=1 to N) and filter processing such as smoothing filter processing is performed. Thereby, up-sampling data DT(n)' having the same size as that of the adjacent (n−1)th data is obtained.

Then, in a subtracting unit 163, subtraction processing is performed between the (n−1)th down-sampling data DT(n−1) and the adjacent (n)th up-sampling data DT(n)'. Thereby, subtraction data DS(0) to DS(N−1) are obtained. These subtraction data DS(0) to DS(N−1) represent data groups including frequency components that are formed by dividing spatial frequency components $f_0$ to $f_N$ included in image data DT(0) into N frequency ranges, respectively. For example, the subtraction data DS(n) (n=0 to N−1) includes frequency components $f_n$ to $f_{n+1}$.

Then, in a multiplying unit 164, subtraction data DS(0), DS(1), . . . , DS(N−1) are multiplied by weighting factors $k_0$, $k_1$, . . . , $k_{N-1}$, respectively. Furthermore, the data DS(n)' (n=1 to N−1) multiplied by the weighting factors are up-sampled in an up-sampling unit 165 so as to have the same data size as that of the original image data DT(0).

Thus equally sized data DS(0) and DS(1)', DS(2)', . . . , DS(N−1)' are added in an adding unit 166. Thereby, data $DT_{EN}$ weighted with respect to each spatial frequency range are generated. Furthermore, the weighted data $DT_{EN}$ and the original image data DT(0) are multiplied by predetermined weighting factors $K_{FR}$ and $(1-K_{FR})$ respectively in a multiplying unit 167, and added to each other in an adding unit 168. Thus, image data $DT_{OUT}$ that has been subjected to the frequency enhancement processing is generated and outputted to the speckle image analysis units 112, 122, 130, 140 and 150, and the image selection unit 113 (FIG. 1). The weighting factors $k_0$ to $k_{N-1}$ to be used in the multiplying unit 164 are set in accordance with the characteristics of the image data to be processed. The weighting factors $k_0$ to $k_{N-1}$ may be stored in the storage unit 103 as shown in FIG. 1 in advance in association with parameters such as the ultrasonic frequency, the depth of the object or observation part, alternatively, the user may input arbitrary values. In the former case, the weighting factors suitable for those parameters are set, and, in the latter case, user-desired frequency enhancement effect can be obtained.

In the case such frequency range division processing is performed on the speckle image data, speckles in large sizes are reduced by making the vicinity of the weighting factors $k_4$ and $k_5$ smaller and suppressing the smaller frequency components. Thereby, an image in which a tissue part is easily viewable can be obtained in the synthesized image. On the other hand, in the case such frequency range division processing is performed on the structure image data, the effect that edges of the structure are made clearer can be obtained by making the vicinity of the weighting factors $k_0$ and $k_1$ larger and emphasizing the larger frequency components.

Further, the speckle image generating unit 111 shown in FIG. 1, and the first and second speckle image generating parts 12c and 12d shown in FIGS. 8 and 11-13 may perform various kinds of image processing other than such frequency range division processing. Specifically, smoothing filter processing, Laplacian filter processing, etc. can be cited.

Next, an ultrasonic imaging apparatus according to the sixth embodiment of the present invention will be described by referring to FIGS. 21-23.

Figure 21:
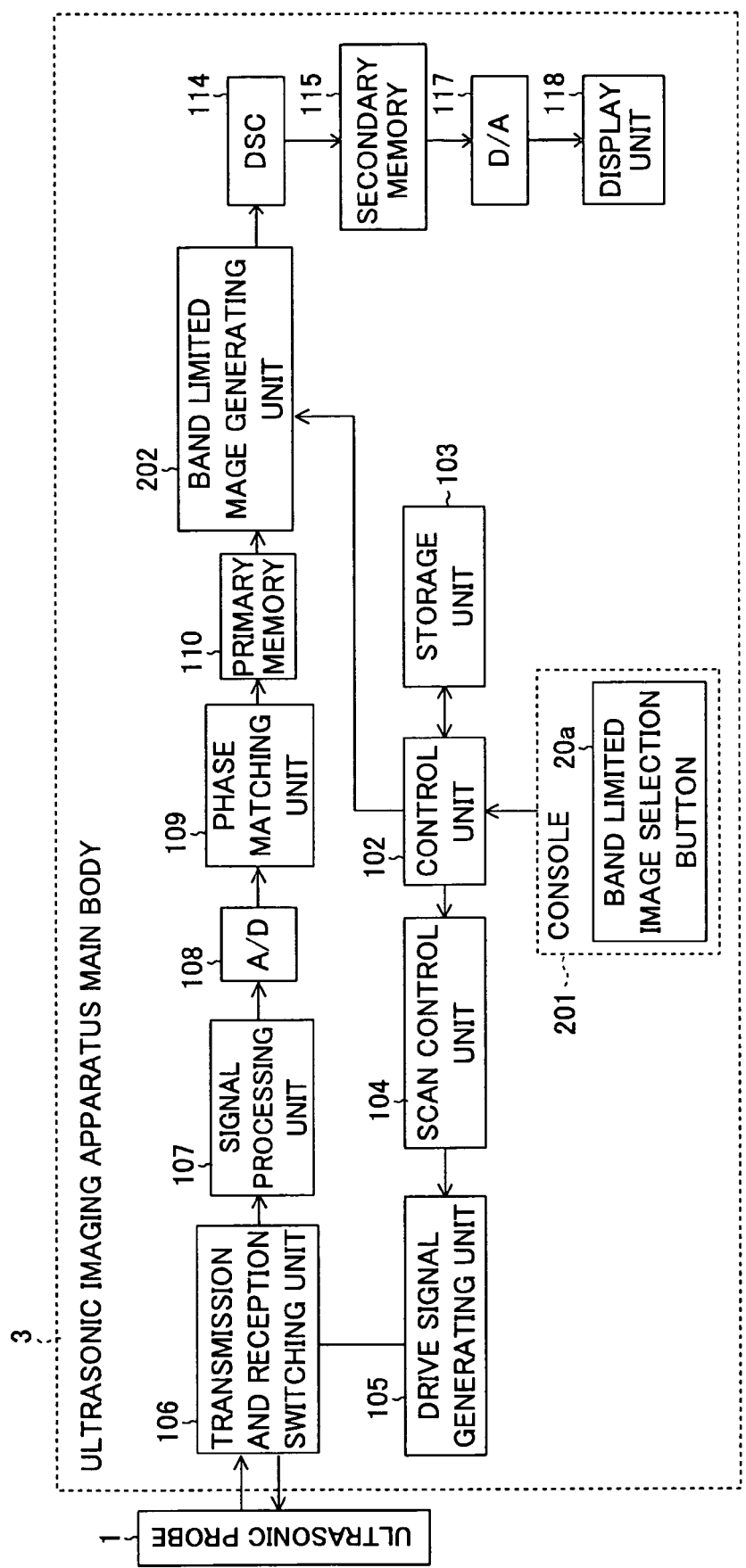
FIG. 21 is a block diagram showing a constitution of an ultrasonic imaging apparatus according to the sixth embodiment of the present invention.

FIG. 21 is a block diagram showing part of the ultrasonic imaging apparatus according to the embodiment. As shown in FIG. 21, the ultrasonic imaging apparatus according to the embodiment includes an ultrasonic probe 1 and an ultrasonic imaging apparatus main body 3. The ultrasonic imaging apparatus main body 3 includes a console 201 in place of the console 101 as shown in FIG. 1, and a band limited image generating unit 202 in place of the speckle analysis section and the image selection unit 113 as shown in FIG. 1. Further, in the ultrasonic imaging apparatus main body 3, the screen synthesizing unit 116 as shown in FIG. 1 is omitted. Other constitution and operation are the same as those in the ultrasonic imaging apparatus shown in FIG. 1.

Of these units, at least the control unit 102, the band limited image generating unit 202 and the DSC 114 form an ultrasonic image processing apparatus according to the embodiment.

The console 201 includes an input device such as a keyboard and touch panel, a pointing device such as a mouse, an adjustment knob, an input button, etc., and is used by a user when various instructions and information are inputted to the ultrasonic imaging apparatus main body. Further, the console 201 is provided with a band limited image selection button 20a operated by the user for inputting signals used for controlling the operation in the band limited image generating unit 202.

The band limited image generating unit 202 generates and outputs band limited image data representing ultrasonic images with spatial frequencies limited in a predetermined band based on image data for one frame representing an ultrasonic image.

Figure 22:
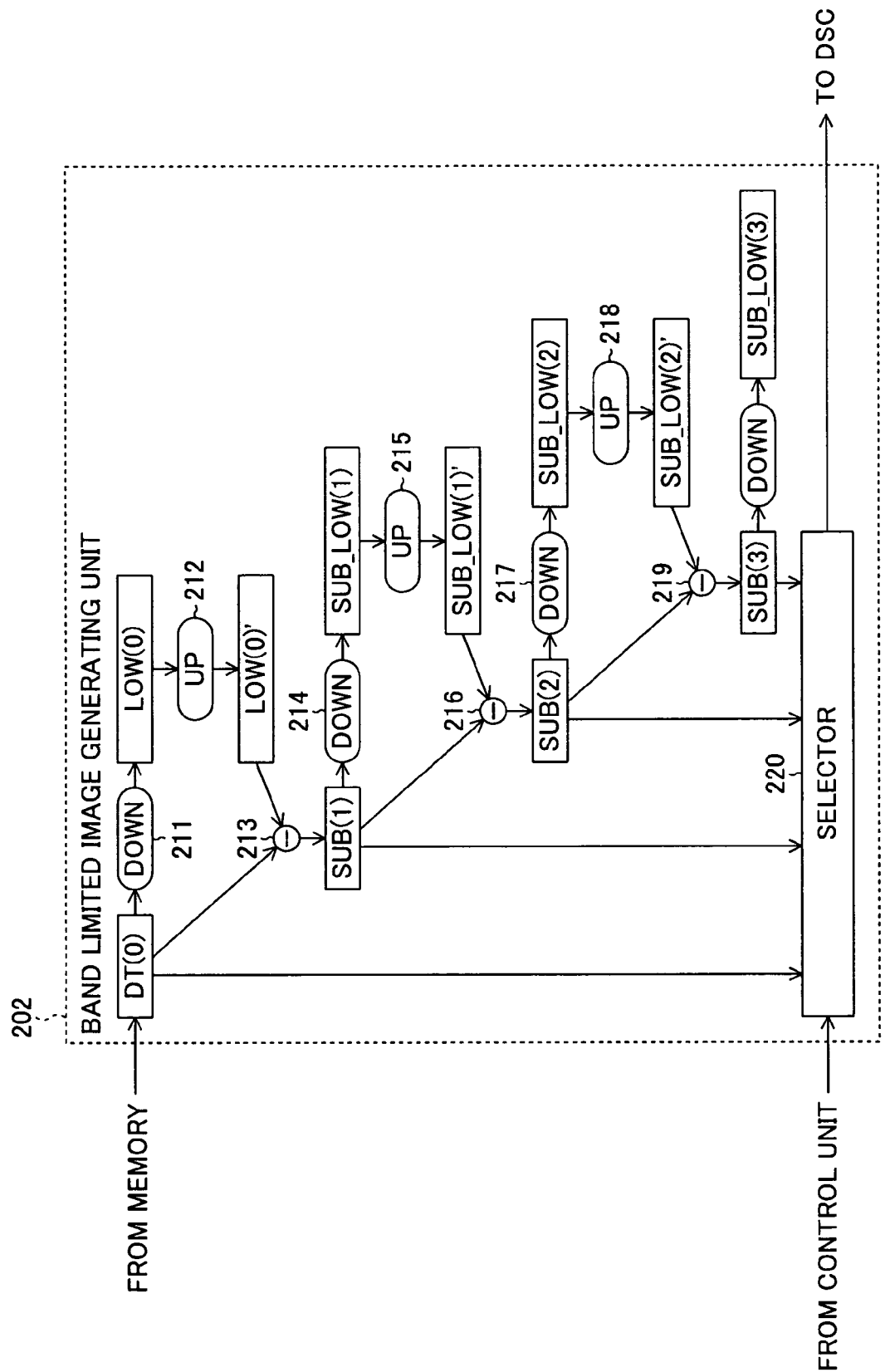
FIG. 22 is a diagram for explanation of the operation of a band limited image generating unit shown in FIG. 21.
Figure 23:
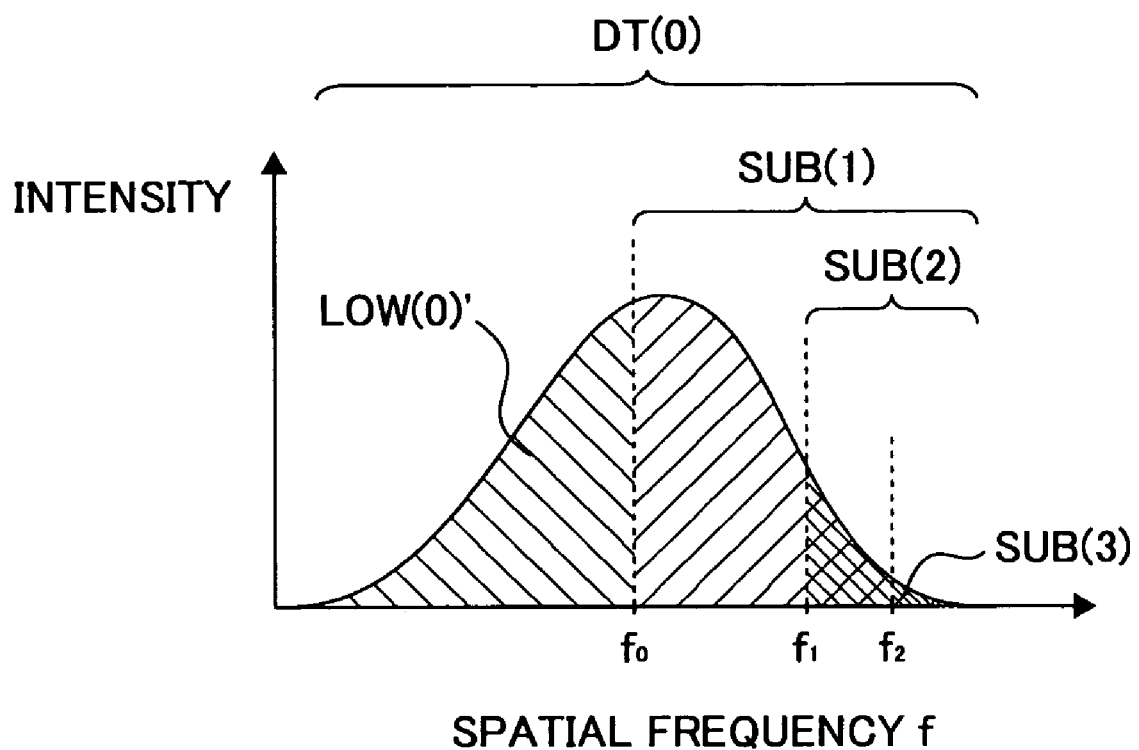
FIG. 23 shows a spatial frequency range of an ultrasonic image represented by image data DT(0)

FIG. 22 is a diagram for explanation of the operation of the band limited image generating unit 202, and FIG. 23 shows a spatial frequency range of an ultrasonic image represented by image data DT(0) for one frame processed in the band limited image generating unit 202. In FIG. 23, a spatial frequency $f_0$ represents a center frequency of a spatial frequency range of the ultrasonic image represented by image data DT(0).

When image data for one frame is accumulated in the primary memory 110 (FIG. 21), the image data is outputted to the band limited image generating unit 202. As shown in FIG. 22, the image data DT(0) for one frame is subjected to thinning processing and filter processing such as Nyquist filter processing in a down-sampling unit 211 (unsharp image processing unit). Thereby, down-sampling data LOW(0) having low spatial frequency components is generated.

Then, the down-sampling data LOW(0) is subjected to processing of inserting data of value "0" and filter processing such as smoothing filter processing in the up-sampling unit 202. Thereby, up-sampling data LOW(0)' having the same size as that of the original image data DT(0) is obtained. The frequency range of the up-sampling data LOW(0)' corresponds to the region where $f<f_0$ within the curve as shown in FIG. 23.

Then, processing of subtracting the up-sampling data LOW(0)' from the image data DT(0) is performed in a subtracting unit (difference processing unit) 213. Thereby, sub-band data SUB(1) is obtained. As shown in FIG. 23, the sub-band data SUB(1) is image data representing an ultrasonic image with spatial frequencies limited to $f \geq f_0$.

Then, the sub-band data SUB(1) is subjected to thinning processing and predetermined filter processing in a down-sampling unit 214. Thus obtained down-sampling SUB_LOW(1) is subjected to processing of inserting data of value "0" and filter processing such as smoothing filter processing in an up-sampling unit 215. Furthermore, in the subtracting unit 16, by performing processing of subtracting thus obtained down-sampling SUB_LOW(1)' from sub-band data SUB(1), sub-band data SUB(2) is obtained. As shown in FIG. 23, the sub-band data SUB(2) is image data representing an ultrasonic having with spatial frequencies limited to $f \geq f_1$. Here, a spatial frequency $f_1$ represents a center frequency of the frequency band where $f \geq f_0$.

Similarly, by performing processing in a down-sampling unit 217, an up-sampling unit 218, and a subtracting unit 219 on the sub-band data SUB(2), sub-band data SUB(3) is obtained. As shown in FIG. 23, the sub-band data SUB(3) is image data representing an ultrasonic image with spatial frequencies limited to $f \geq f_2$. Here, spatial frequency $f_2$ is a center frequency of the frequency band where $f \geq f_1$.

Furthermore, by sequentially performing such processing, sub-band data SUB(4), SUB(5), . . . are obtained.

A selector 220 selects one of the image data DT(0), the sub-band data SUB(1), the sub-band data SUB(2), . . . and output the data according to the band limited image selection signal outputted from the control unit 102.

Referring to FIG. 21 again, the operation of the ultrasonic imaging apparatus according to the embodiment will be described.

Prior to the start of ultrasonic imaging, the user selects the band limited image selection button of the console 201 to display images with limited spatial frequencies to a preferred band on the screen. In response thereto, the band limited image selection signal is outputted to the band limited image generating unit 202 from the control unit 102.

Then, when the user starts ultrasonic imaging, the control unit 102 outputs control signals for starting ultrasonic imaging to the respective units. In response, the ultrasonic probe 1 transmits and receives ultrasonic waves and image data corresponding to the reception signals of the ultrasonic waves are stored in the primary memory 110. Then, when image data for one frame is accumulated in the primary memory 110, the image data is outputted to the band limited image generating unit 202.

In the band limited image generating unit 202, as has been described by referring to FIG. 22, sub-band data SUB(1), SUB(2), . . . representing the band limited image with spatial frequencies limited to a predetermined band are generated. Then, the data selected by the user from those sub-band data SUB(1), SUB(2), . . . and the original image data DT(0) is outputted to the DSC 114. The data outputted from the band limited image generating unit 202 is subjected to conversion processing of scan format in the DSC 114, once stored in the secondary memory 115, converted into analog image signals in the D/A converter 117, and supplied to the display unit 118. Thereby, moving or still image of the band limited image with spatial frequencies limited to a band of user's preference or the original ultrasonic image is displayed on the display unit 118.

The user can display different band limited images on the display unit 118 by switching the command using the band limited image selection button 111a even while the band limited image or the original ultrasonic image is displayed on the display unit 118.

As described above, according to the embodiment, since band limited image data is generated by down-sampling processing and subtraction (difference) processing, high-speed processing can be performed and the band limited images can be displayed nearly in real time. Further, the console is provided with the band limited image selection button, and thereby, the band limited image with spatial frequencies limited to a band of user's preference or the original ultrasonic image can be displayed. Therefore, in the clinical use of medical diagnoses, the user can display a moving image of band limited images in which a speckle pattern clearly appears by switching the band of the band limited images, and efficiently determine the tissue properties of the part to be observed within the object based on the band limited images. Thus, the ultrasonic imaging apparatus according to the embodiment can be effectively utilized for diagnostic support.

Next, an ultrasonic imaging apparatus according to the seventh embodiment of the present invention will be described by referring to FIGS. 24-25C.

Figure 24:
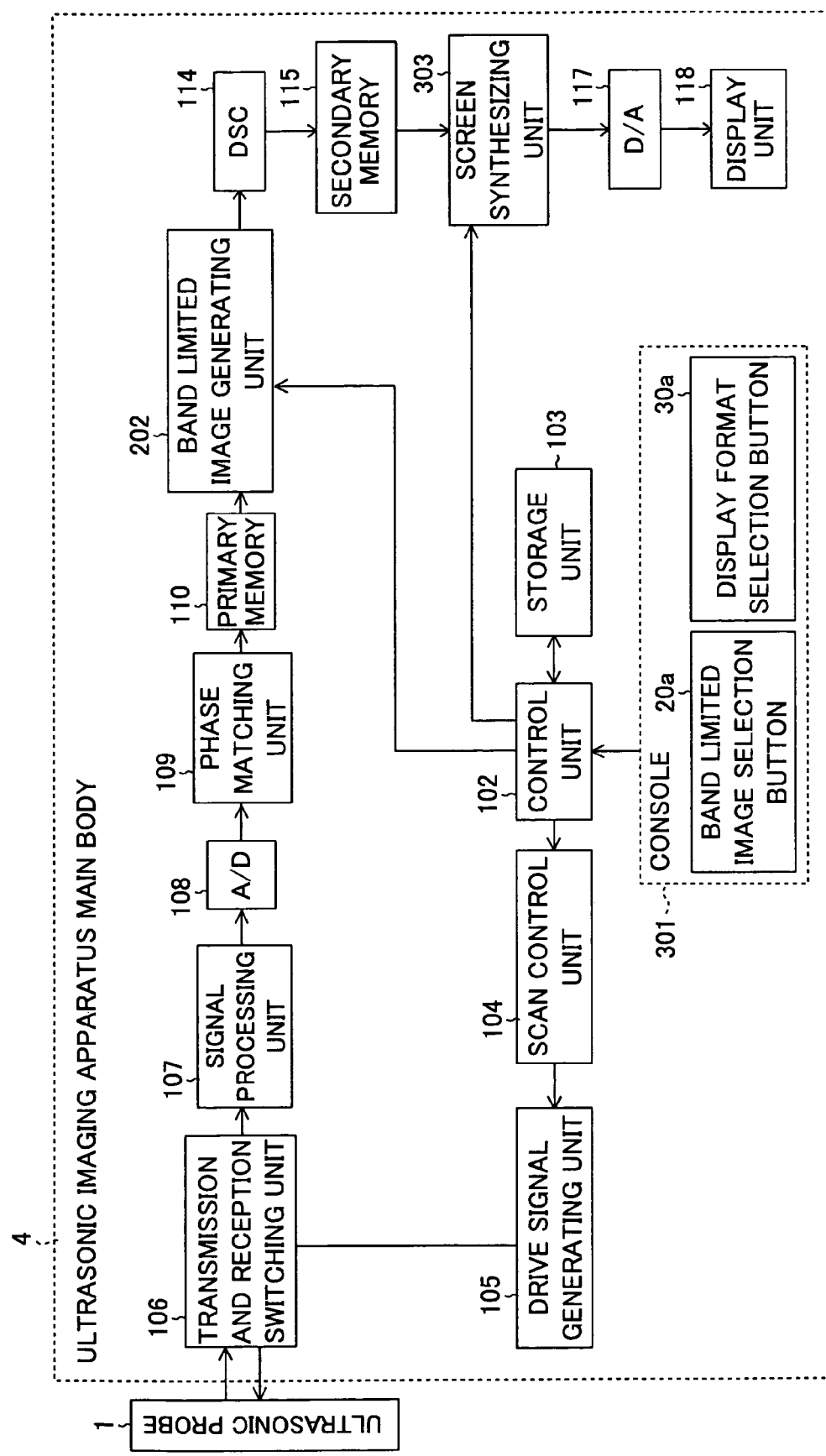
FIG. 24 is a block diagram showing a constitution of an ultrasonic imaging apparatus according to the seventh embodiment of the present invention.

FIG. 24 is a block diagram showing part of the ultrasonic imaging apparatus according to the embodiment. As shown in FIG. 24, the ultrasonic imaging apparatus according to the embodiment includes an ultrasonic probe 1 and an ultrasonic imaging apparatus main body 4. The ultrasonic imaging apparatus main body 4 includes a console 301 and a DSC 302 in place of the console 201 and the DSC 114 as shown in FIG. 21, respectively, and further includes a screen synthesizing unit 303. Other constitution and operation are the same as those in the ultrasonic imaging apparatus as shown in FIG. 21.

Of these units as shown in FIG. 24, at least the control unit 102, the band limited image generating unit 202 and the DSC 302 form an ultrasonic image processing apparatus according to the embodiment. Furthermore, the ultrasonic image processing apparatus may include the screen synthesizing unit 303.

The console 301 is further provided with a display format selection button 30a in addition to the band limited image selection button 20a for selecting a frequency range. The display format selection button 30a is used when a user inputs the display format of the synthesized screen, which will be described later.

The DSC 302 generates image data for display representing normal ultrasonic images and image data for display representing band limited images by respectively converting scan formats with respect to both the image data representing normal ultrasonic image with unlimited spatial frequencies and band limited image data outputted from the band limited image generating unit 202. These image data are stored in the secondary memory 115.

The screen synthesizing unit 303 creates a synthesized screen containing two ultrasonic images based on two kinds of image data generated in the DSC 302 according to the display format selection signal outputted from the control unit 102, and generates synthesized image data. The display format selection signal is outputted from the control unit 102 as the user selects a desired display format by using the display format selection button 30a.

Figure 25A:
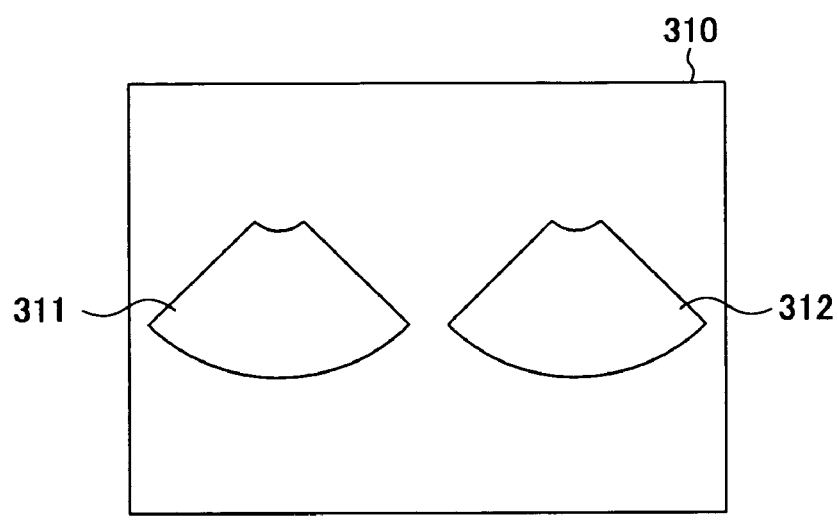
FIGS. 25A to 25C show display formats created in a screen synthesizing unit shown in FIG. 24.
Figure 25B:
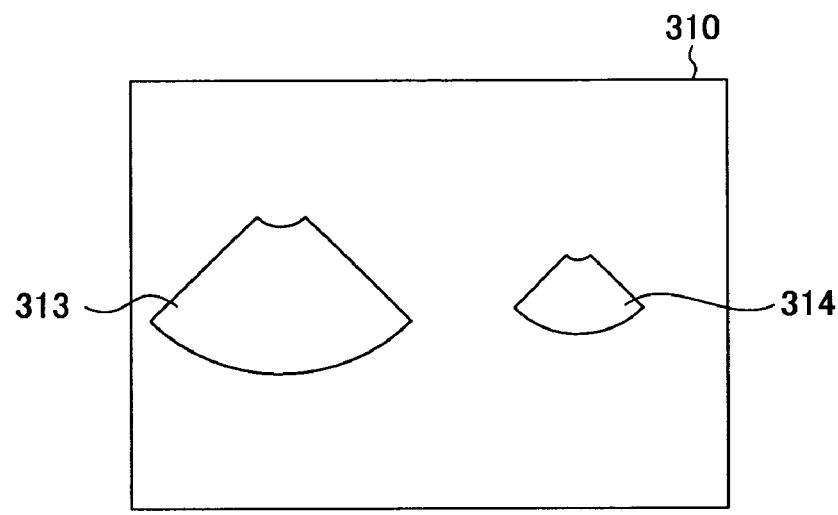
Figure 25C:
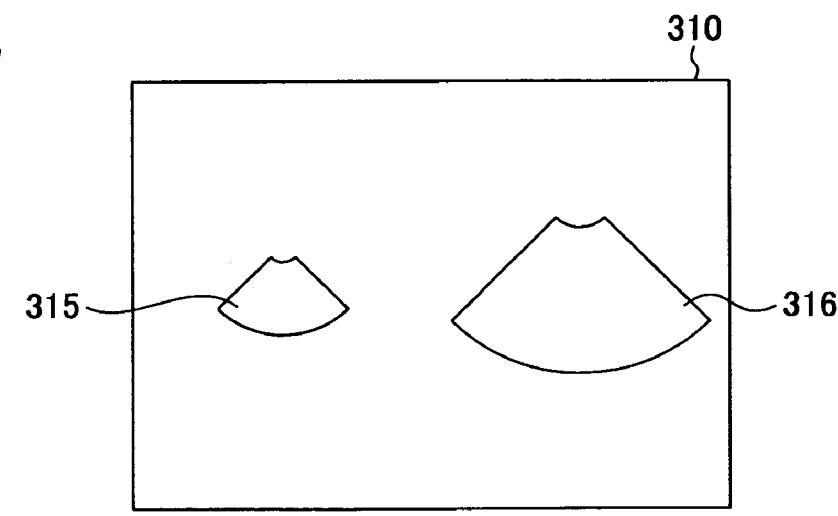

As the display formats of synthesized screen created in the screen synthesizing unit 303, for example, the formats as shown in FIGS. 25A-25C are conceivable. That is, as shown in FIG. 25A, a normal ultrasonic image 311 and a band limited image 312 may be displayed side-by-side in the same size on a screen 310 of the display unit. Further, as shown in FIG. 25B, a normal ultrasonic image 313 is displayed in a larger size and a band limited image 314 is displayed in a smaller size side-by-side. Such a display format is suitable for the case where the user wishes to observe a part to be observed in detail with the normal ultrasonic image 313 while referring to the presence or absence of a speckle pattern or the like with the band limited image 314. Furthermore, as shown in FIG. 25C, a normal ultrasonic image 315 is displayed in a smaller size and a band limited image 314 is displayed in a larger size side-by-side. Such a display format is suitable for the case where the user wishes to observe the condition of a speckle pattern in detail with the band limited image 314 while confirming the position and shape of a part to be observed by referring to the normal ultrasonic image 315.

As described above, according to the embodiment, since both a normal ultrasonic image with unlimited spatial frequency and a band limited image of user's preference can be displayed on a screen in a display format of user's preference, the efficiency of medical diagnoses can be further improved.

Next, an ultrasonic imaging apparatus according to the eighth embodiment of the present invention will be described by referring to FIGS. 26-28C.

Figure 26:
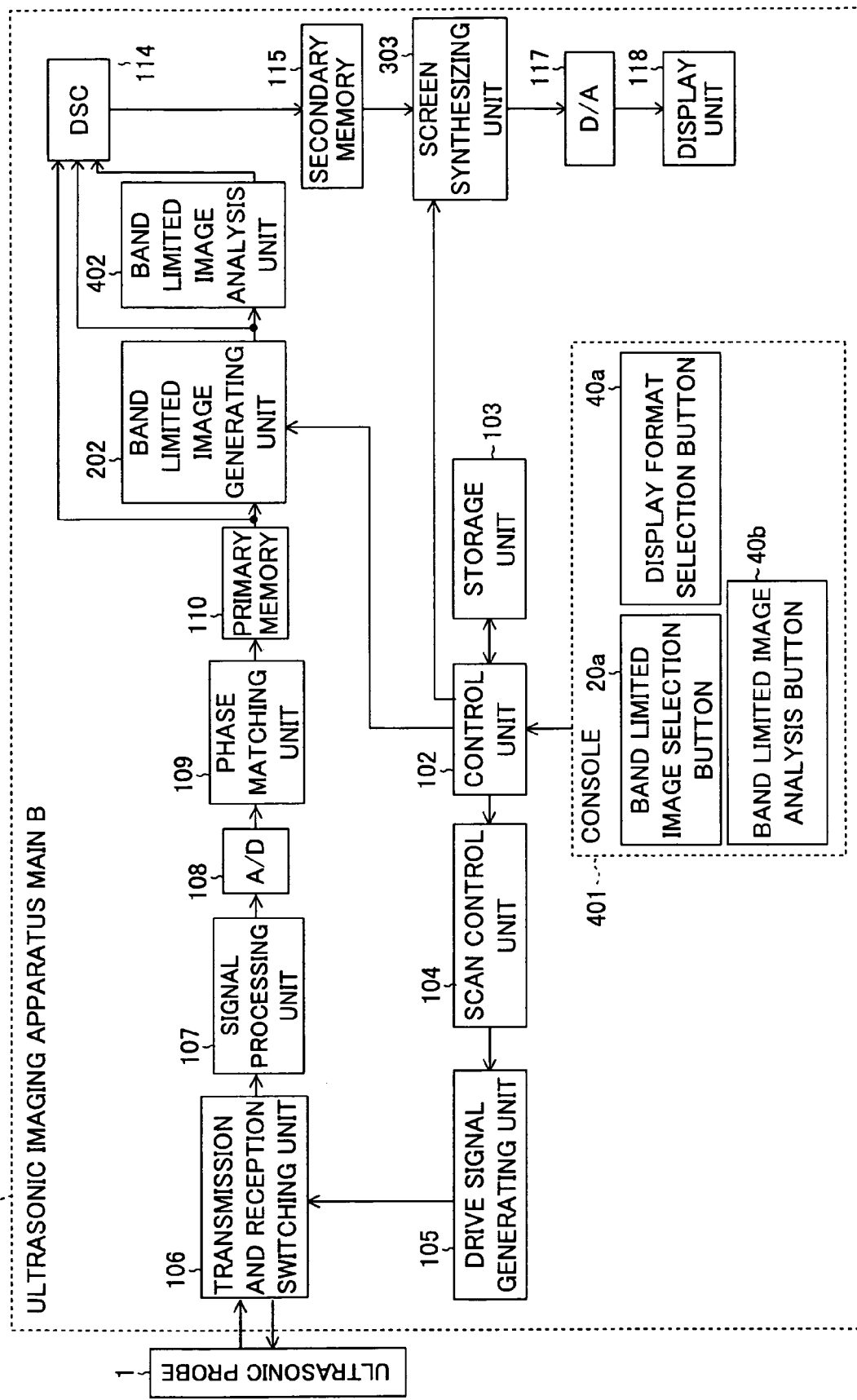
FIG. 26 is a block diagram showing a constitution of an ultrasonic imaging apparatus according to the eighth embodiment of the present invention.

FIG. 26 is a block diagram showing part of the ultrasonic imaging apparatus according to the embodiment. As shown in FIG. 26, the ultrasonic imaging apparatus according to the embodiment includes an ultrasonic probe 1 and an ultrasonic imaging apparatus main body 5. The ultrasonic imaging apparatus main body 5 includes a console 401 and a DSC 403 in place of the console 201 and the DSC 114 as shown in FIG. 21, respectively, and further includes a band limited image analysis unit 402 and a screen synthesizing unit 404. Other constitution and operation are the same as those in the ultrasonic imaging apparatus as shown in FIG. 21.

Of these units as shown in FIG. 26, at least the control unit 102, the band limited image generating unit 202, the band limited image analysis unit 402 and the DSC 403 form an ultrasonic image processing apparatus according to the embodiment. Furthermore, the ultrasonic image processing apparatus may include the screen synthesizing unit 404.

The console 401 is further provided with a display format selection button 40a to be used for a user to input the display format of the synthesized screen and a band limited image analysis button 40b in addition to the band limited image selection button 20a for selecting a frequency range. The band limited image analysis button 40b is used when the user inputs a command as to whether or not analysis of band limited image is performed.

The band limited image analysis unit 402 analyzes a band limited image represented by band limited image data outputted from the band limited image generating unit 202.

Figure 27:
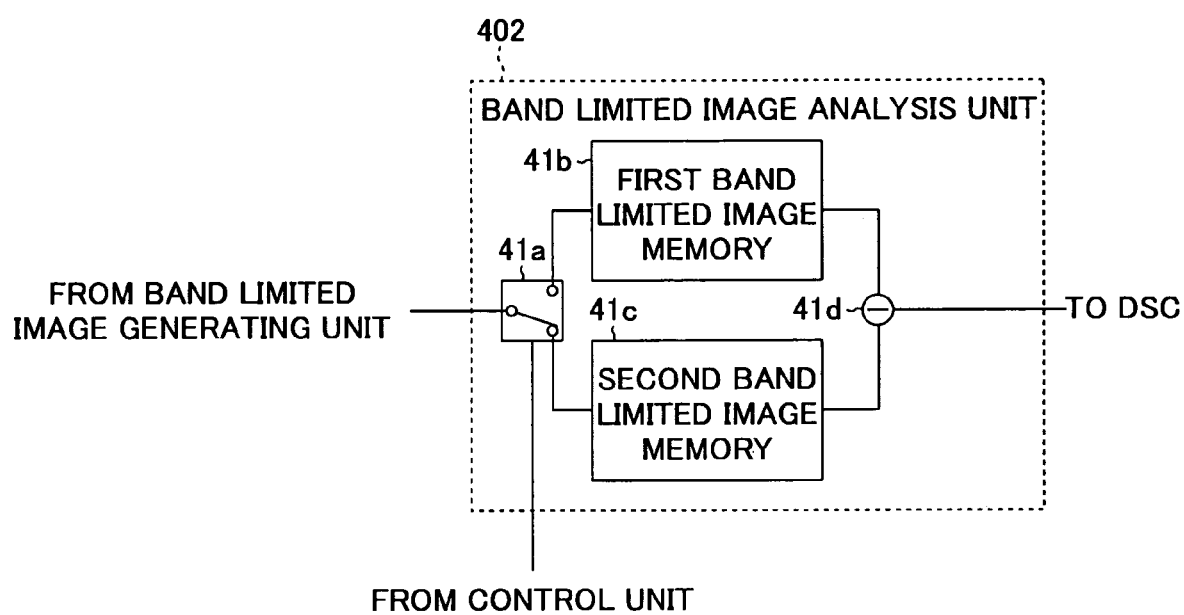
FIG. 27 is a block diagram showing a constitution of a band limited image analysis unit shown in FIG. 26.

FIG. 27 is a block diagram showing a constitution of the band limited image analysis unit 402 as shown in FIG. 26. As shown in FIG. 27, the band limited image analysis unit 402 includes a switch 41a, a first band limited image memory 41b, a second band limited image memory 41c and a subtraction part 41d. The switch 41a selects one of output destinations of data from the band limited image generating unit 202 under the control of the control unit 102 to allow the first band limited image memory 41b and the second band limited image memory 41c to alternately store band limited image data for one frame sequentially outputted from the band limited image generating unit 202. The subtraction part 41d generates frame difference data by performing subtraction between band limited image data stored in those memories when the band limited image data is updated in the first band limited image memory 41b or the second band limited image memory 41c. The frame difference data represents time-dependent change of the band limited image data and is outputted to the DSC 403 as band limited image analysis data.

Referring to FIG. 26 again, the DSC 403 converts the respective scan formats of the image data for one frame stored in the primary memory 110 and representing normal ultrasonic images, the band limited image data outputted from the band limited image generating unit 202, and the band limited image analysis data outputted from the band limited image analysis unit 402 to generate image data for display representing normal ultrasonic images, image data for display representing band limited images, and image data for display representing analysis results of the limited images. These kinds of image data are stored in the secondary memory 115.

The screen synthesizing unit 404 creates a synthesized screen containing one to three ultrasonic image(s) based on three kinds of image data generated in the DSC 403 according to the display format selection signal outputted from the control unit 102 to generate synthesized image data. The display format selection signal is outputted from the control unit 102 as the user selects a desired display format by using the band limited image selection button 40a.

Figure 28A:
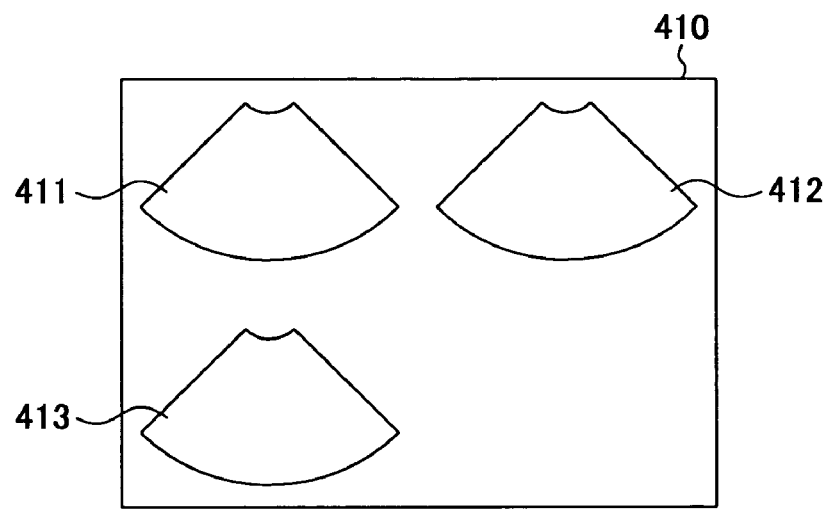
FIGS. 28A to 28C show display formats created in a screen synthesizing unit shown in FIG. 26.
Figure 28B:
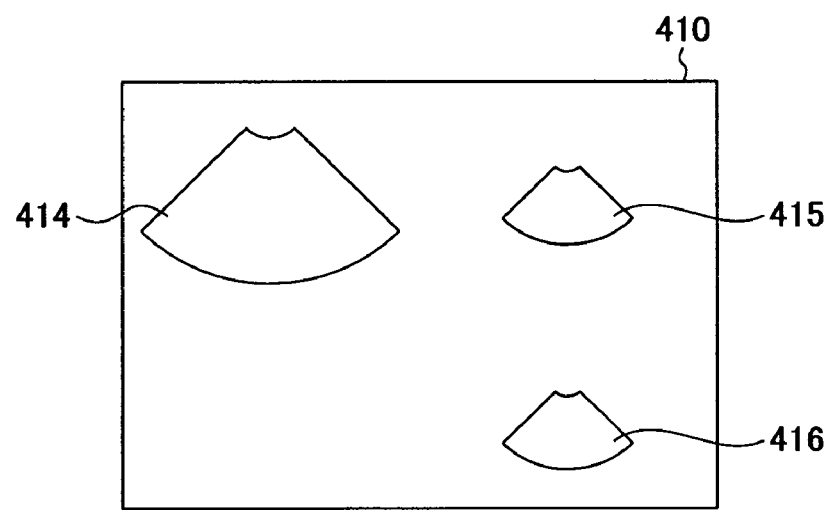
Figure 28C:
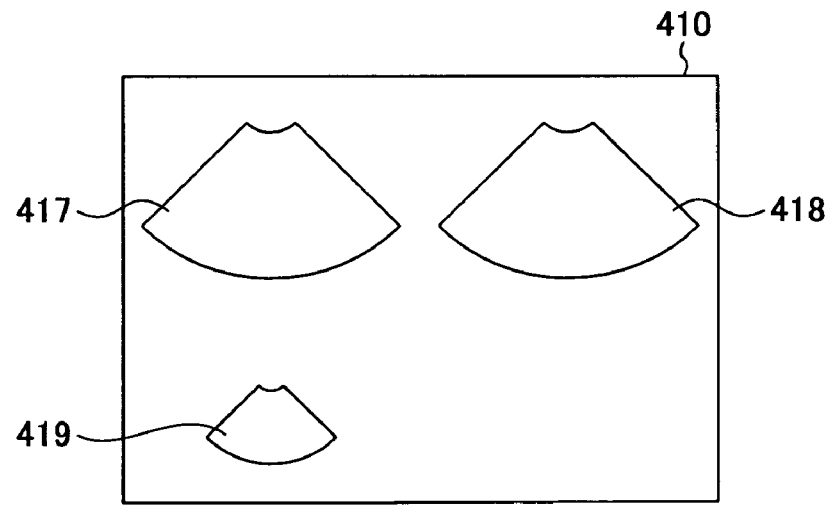

As the display formats of synthesized screen created in the screen synthesizing unit 404, the format in which only one of the normal ultrasonic image, the band limited image, and the analysis image representing the analysis result thereof is displayed (single display), or two of them are displayed (dual display) may be used. In the latter case, for example, the formats as shown in FIGS. 25A-25C may be used. Alternatively, the format in which all of the normal ultrasonic image, the band limited image and the analysis image are displayed (triple display) may be used. In the case of triple display, for example, as shown in FIG. 28A, a normal ultrasonic image 411, a band limited image 412, and an analysis image 413 may be displayed in the same size. Further, as shown in FIG. 28B, only one of the three images (e.g., an analysis image 414) may be displayed in a larger size, and the rest two images (e.g., a normal ultrasonic image 415 and a band limited image 416) may be displayed in a smaller size. Such a display format is suitable for the case where the user wishes to observe the analysis image detail while confirming the position and shape of a part to be observed by referring to the band limited image and the normal ultrasonic image. Furthermore, as shown in FIG. 28C, two of the three images (e.g., a band limited image 417 and an analysis image 418) may be displayed in a larger size, and the rest one image (e.g., a normal ultrasonic image 419) may be displayed in a smaller size. Such a display format is suitable for the case where the user wishes to observe the condition of a speckle pattern and the change according to time thereof in detail represented in the band limited image and the analysis image while confirming the position and shape of apart to be observed by referring to the normal ultrasonic image.

As described above, according to the embodiment, since the features of the band limited image are analyzed by obtaining the time-dependent change of the band limited image, a part with drastic time-dependent change of speckle pattern can be distinguished easily. Therefore, when the tissue properties of the part to be observed is determined based on the speckle pattern, the determination becomes easier, and the quality and efficiency of medical diagnoses can be improved. Further, according to the embodiment, since whether the analysis of band limited image is performed or not can be selected or the pattern of the size of images to be displayed on the screen can be selected according to the preference of user, the ultrasonic imaging apparatus becomes user-friendly, and the apparatus can be effectively utilized for diagnostic support.

Next, an ultrasonic imaging apparatus according to the ninth embodiment of the present invention will be described by referring to FIGS. 29 and 30.

Figure 29:
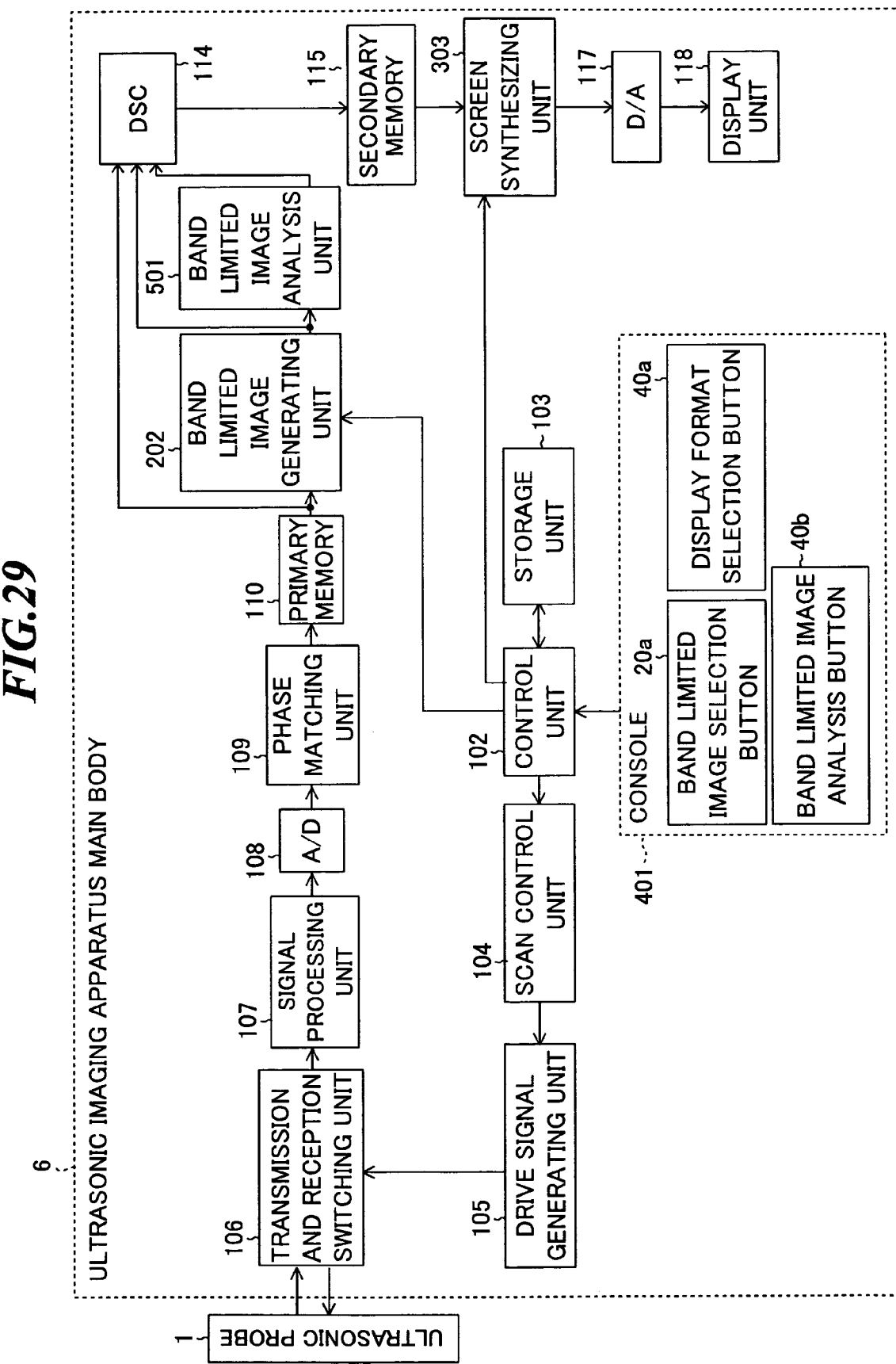
FIG. 29 is a block diagram showing a constitution of an ultrasonic imaging apparatus according to the ninth embodiment of the present invention.
Figure 30:
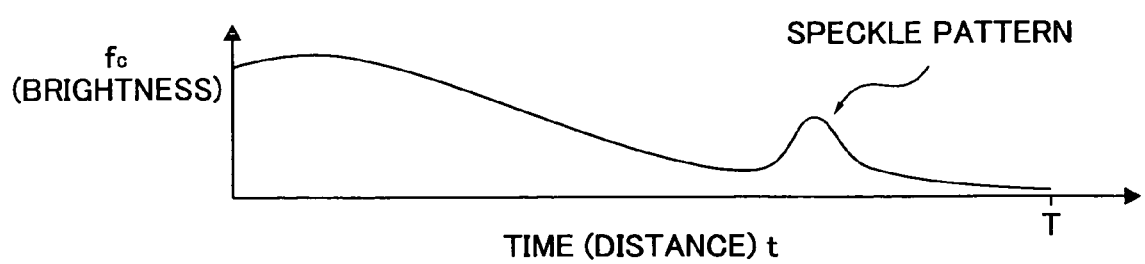
FIG. 30 is a diagram for explanation of frequency processing performed in a band limited image analysis unit shown in FIG. 29.

FIG. 29 is a block diagram showing part of the ultrasonic imaging apparatus according to the embodiment. As shown in FIG. 29, the ultrasonic imaging apparatus according to the embodiment includes an ultrasonic probe 1 and an ultrasonic imaging apparatus main body 6. The ultrasonic imaging apparatus main body 6 includes a band limited image analysis unit 501 in place of the band limited image analysis unit 402 as shown in FIG. 26. Other constitution and operation are the same as those in the ultrasonic imaging apparatus shown in FIG. 26.

The band limited image analysis unit 501 analyzes the band limited image by using frequency processing. The frequency processing is the same as that described referring to FIGS. 10A-10C in the second embodiment.

Here, as shown in FIG. 10C, the deeper the part, the greater the spatial frequency attenuates. The reason is that, since relatively high frequency components of ultrasonic waves propagating the object are easier to be scattered and ultrasonic echo signals from the deep part mainly includes relatively low frequency components, the deeper the part, the lower the resolving power becomes.

Accordingly, by further making an analysis with respect to the spatial frequency in a band limited image in which the spatial frequency range is limited to some degree, a region characterized by having a high spatial frequency such as a speckle pattern can be clearly displayed. That is, as shown in FIG. 30, the spatial frequency attenuates according to the depth in the band limited image, however, when a speckle pattern exists in a region at a certain depth, the region is displayed with high brightness even when the region is located deep.

Thus, in the embodiment, since a region, in which specific frequency attenuation is seen, is displayed with high brightness, such region can be distinguished easily. Therefore, this function is effective for diagnostic support because the determination becomes easier when medical diagnoses are made based on speckle patterns, or the like.

Next, an ultrasonic imaging apparatus according to the tenth embodiment of the present invention will be described by referring to FIGS. 31-32B.

Figure 31:
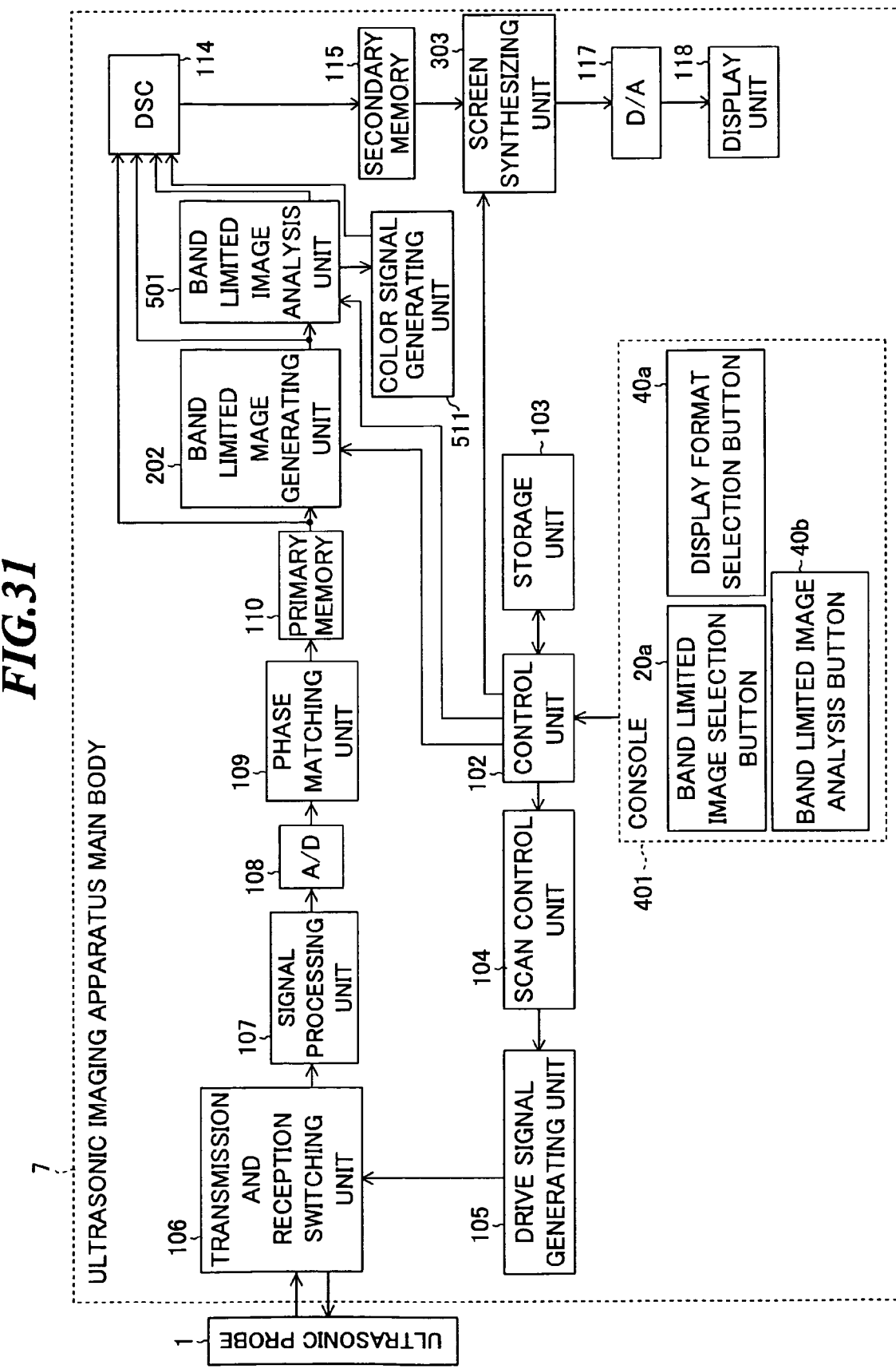
FIG. 31 is a block diagram showing a constitution of an ultrasonic imaging apparatus according to the tenth embodiment of the present invention.

FIG. 31 is a block diagram showing part of the ultrasonic imaging apparatus according to the embodiment. The ultrasonic imaging apparatus according to the embodiment includes an ultrasonic probe 1 and an ultrasonic imaging apparatus main body 7. The ultrasonic imaging apparatus main body 7 includes a band limited image analysis unit 510 in place of the band limited image analysis unit 501 as shown in FIG. 29, and further includes a color signal generating unit 511. Other constitution and operation are the same as those in the ultrasonic imaging apparatus shown in FIG. 29.

Figure 32A:
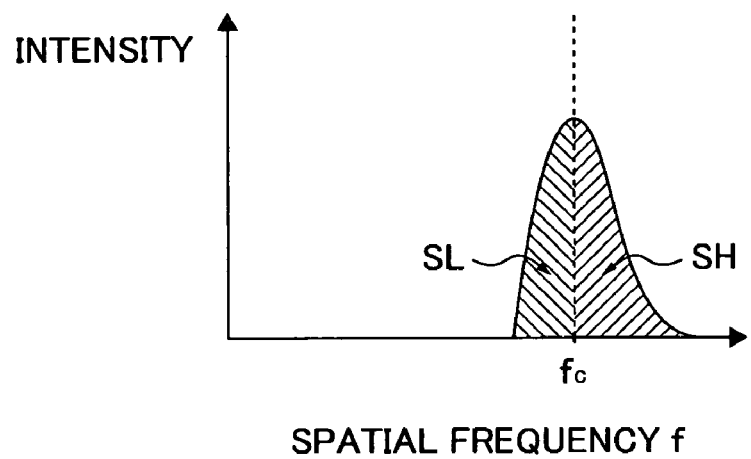
FIGS. 32A and 32B are diagrams for explanation of frequency processing performed in the band limited image analysis unit shown in FIG. 29.
Figure 32B:
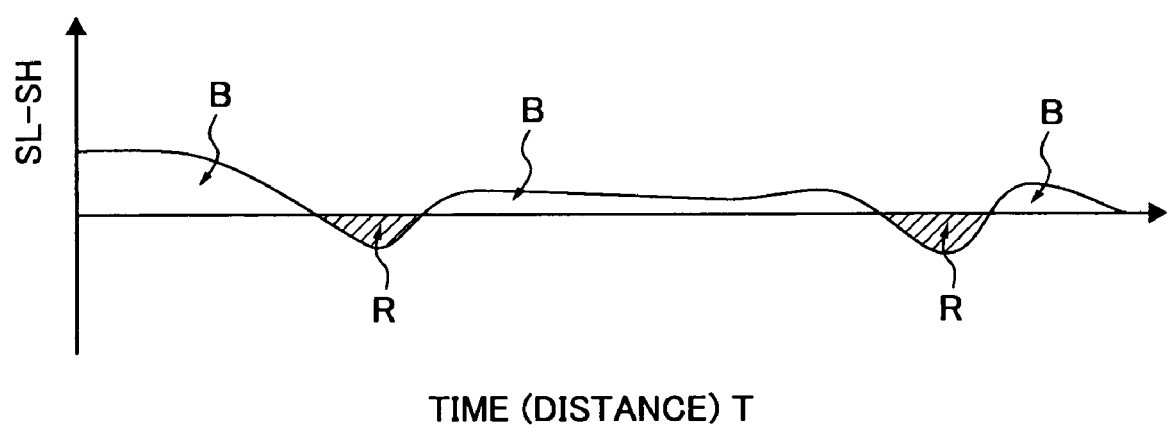

The band limited image analysis unit 510 analyzes a band limited image by using frequency processing that has been described by referring to FIGS. 10A-10C. In this regard, The difference (SL−SH) between integration value SL in a range less than the center frequency or peak frequency $f_c$ and integration value SH in a range equal to or more than the center frequency or peak frequency $f_c$ is used as a representative value (feature quantity) at time $t_0$ as shown in FIG. 32A. In this case, as shown in FIG. 32B, an analysis result represented by positive or negative values is obtained according to the spatial frequency distribution in the interval of the window width "W" (FIG. 10A).

Furthermore, the band limited image analysis unit 510 generates band limited image analysis data based on the difference (SL−SH) in the analysis result. That is, color signals are assigned to the analysis image according to the positive or negative of the difference (SL−SH) and the absolute values of the difference values |SL−SH| are converted into brightness values. Specifically, blue color signals are assigned to regions where (SL−SH)>0 (regions "B" as shown in FIG. 32B), and red color signals are assigned to regions where (SL−SH)<0 (regions "R" as shown in FIG. 32B). The assignment of color signals is performed in the color signal generating unit 511 based on the analysis result in the band limited image analysis unit 510.

An image represented by performing DSC processing on the band limited image analysis data expresses depth-dependent change of high and low frequency difference contained in the band limited image.

Here, as has been described above, since the deeper the part, the greater the spatial frequency attenuates in the ultrasonic image, the low spatial frequency components are normally dominant and the difference (SL−SH) becomes positive. However, in a region having high spatial frequency components such as a speckle pattern, the high spatial frequency components are normally dominant and the difference (SL−SH) becomes negative.

In the embodiment, since the region, where such specific frequency attenuation is seen, is displayed in a different color (e.g., red relative to blue), such a region can be distinguished easily, and the function can be effectively utilized for diagnostic support when medical diagnoses are performed based on speckle patterns.

Next, an ultrasonic imaging apparatus according to the eleventh embodiment of the present invention will be described by referring to FIGS. 29 and 33.

Figure 33:
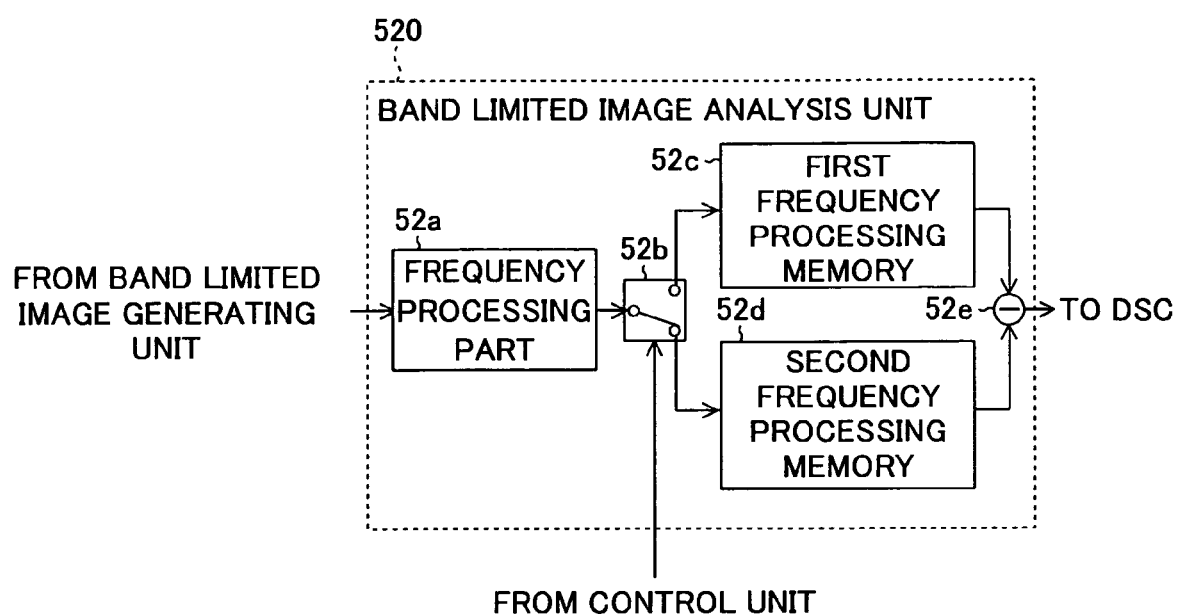
FIG. 33 is a block diagram showing a constitution of a band limited image unit included in an ultrasonic imaging apparatus according to the eleventh embodiment of the present invention.

The ultrasonic imaging apparatus according to the embodiment includes a band limited image analysis unit 520 as shown in FIG. 33 in place of the band limited image analysis unit 501 as shown in FIG. 29. Other constitution and operation are the same as those in the ultrasonic imaging apparatus as shown in FIG. 29.

As shown in FIG. 33, the band limited image analysis unit 520 includes a frequency processing part 52a, a switch 52b, a first frequency processing memory 52c, a second frequency processing memory 52d and a subtraction part 52e.

The frequency processing part 52a generates analysis data representing depth-dependent change of spatial frequency components contained in the band limited image by performing waveform/frequency transform processing with respect to each line on the band limited image data outputted from the band limited image generating unit 202. The frequency processing and the operation of generating analysis data of the band limited image in the frequency processing part 52a are the same as those described in the ninth embodiment of the present invention.

The switch 52b selects one of output destinations of data from the frequency processing part 52a under the control of the control unit 102 to allow the first frequency processing memory 52c and the second frequency processing memory 52d to alternately store analysis data for one frame sequentially outputted from the frequency processing part 52a. The subtraction part 52e generates frame difference data by performing subtraction between analysis data respectively stored in those memories when the analysis data is updated in the first frequency processing memory 52c or the second frequency processing memory 52d. The frame difference data is outputted to the DSC 403 as band limited image analysis data.

Thus, time-dependent change of the depth-dependent change of the spatial frequency components contained in the band limited image can be imaged by obtaining differences between frames of the analysis data that has been obtained by performing frequency processing on the band limited image. Therefore, this function is effective for diagnostic support when medical diagnoses are made based on speckle patterns because a part where specific frequency attenuation appears in a specific pattern and the time-dependent change of speckle pattern is drastic can be distinguished easily, for example.

As a modified example of the ultrasonic imaging apparatus according to the present invention, when the analysis data is generated in the frequency processing part 52a, the difference (SL−SH) may be used as a representative value at time $t_0$ like in the tenth embodiment (FIGS. 32A and 32B) of the present invention. In this case, band limited image analysis data is generated by performing frame difference processing on the difference (SL−SH) obtained by frequency processing, assigning color signals according to positive and negative of values after frame difference processing, and converting the absolute values after frame difference processing into brightness values.

Next, an ultrasonic imaging apparatus according to the twelfth embodiment of the present invention will be described by referring to FIGS. 34-37.

Figure 34:
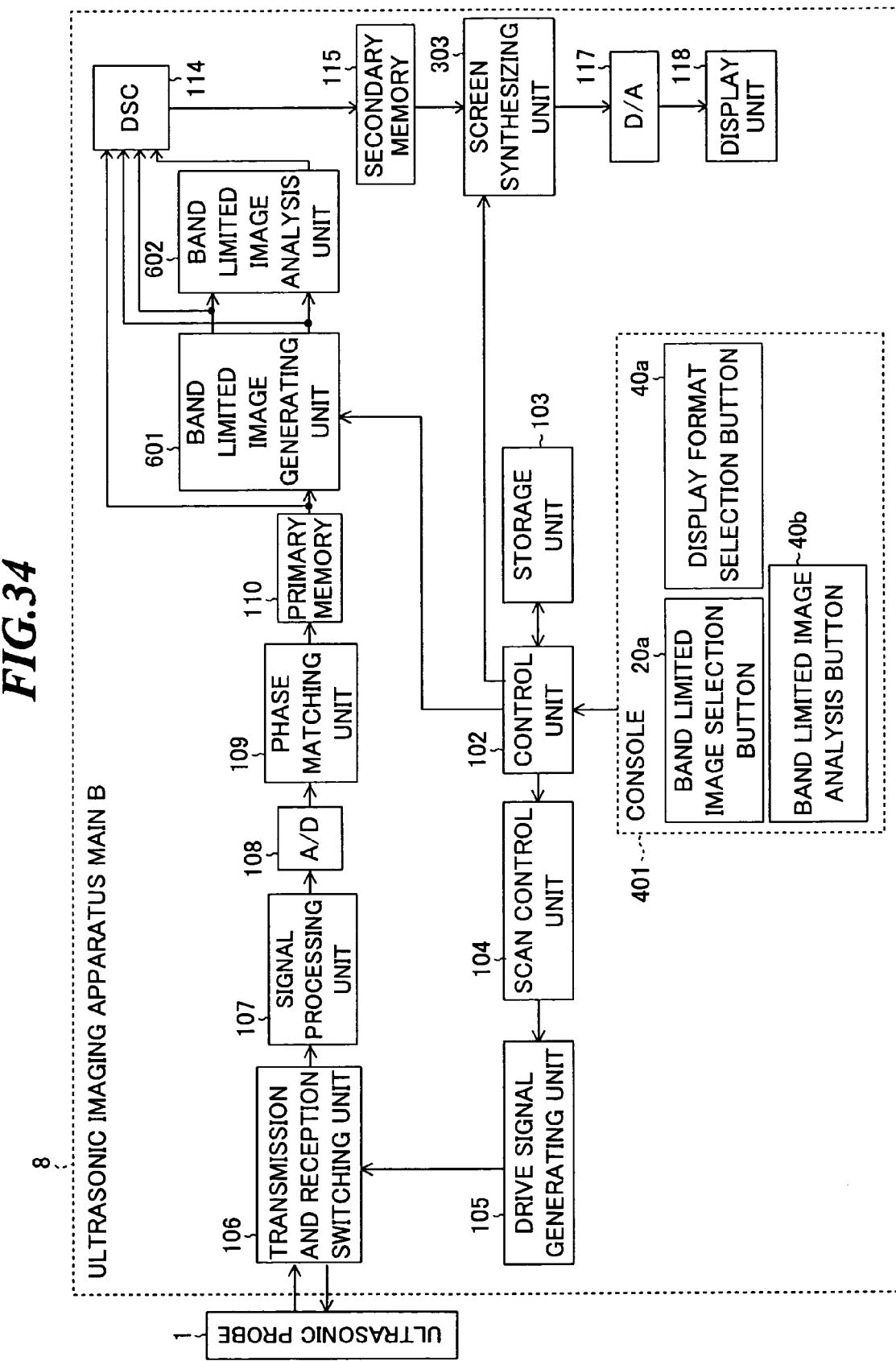
FIG. 34 is a block diagram showing a constitution of an ultrasonic imaging apparatus according to the twelfth embodiment of the present invention.

FIG. 34 is a block diagram showing part of the ultrasonic imaging apparatus according to the embodiment. As shown in FIG. 34, the ultrasonic imaging apparatus according to the embodiment includes an ultrasonic probe 1 and an ultrasonic imaging apparatus main body 8. The ultrasonic imaging apparatus main body 8 includes a band limited image generating unit 601 and a band limited image analysis unit 602 in place of the band limited image generating unit 202 and the band limited image analysis unit 402 as shown in FIG. 26. Other constitution and operation are the same as those in the ultrasonic imaging apparatus shown in FIG. 26.

The band limited image generating unit 601 generates and outputs band limited image data having different frequency range from each other based on image data for one frame representing an ultrasonic image.

Figure 35:
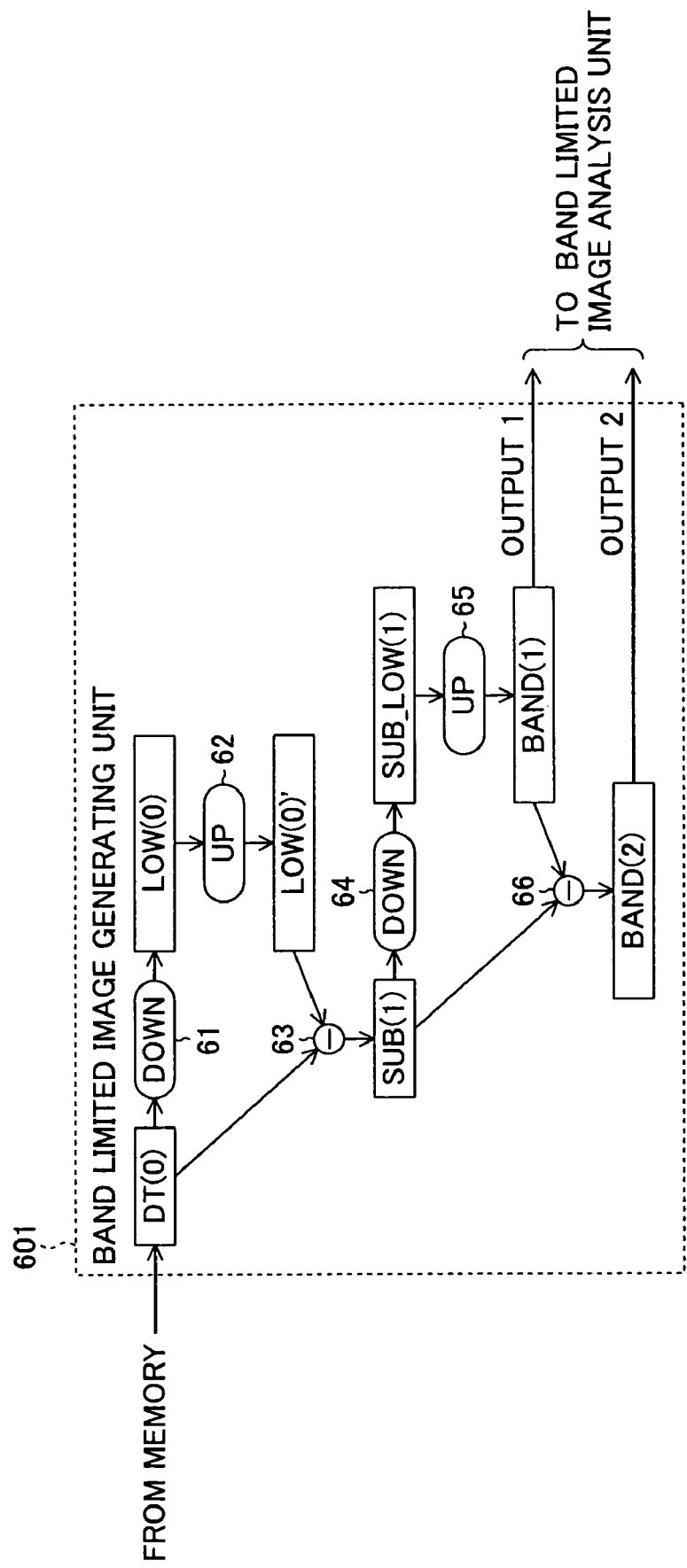
FIG. 35 is a diagram for explanation of frequency processing performed in a band limited image analysis unit shown in FIG. 34.
Figure 36:
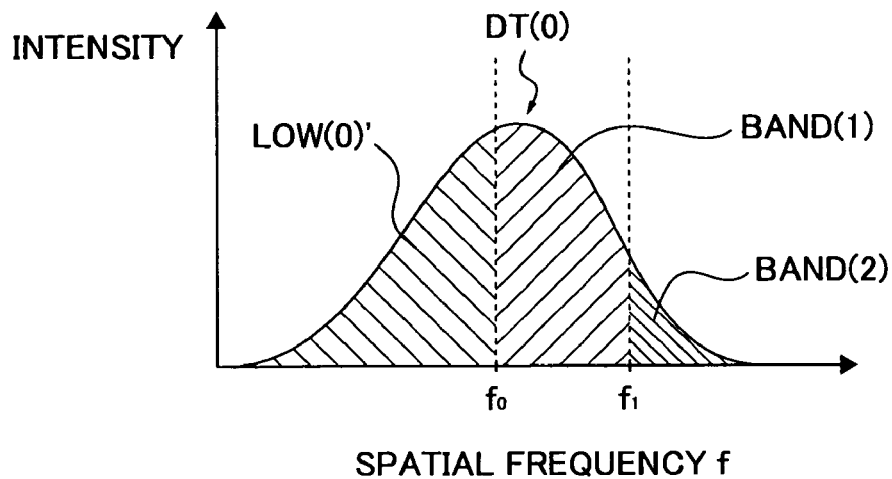
FIG. 36 shows a spatial frequency range of an ultrasonic image represented by image data DT(0)

FIG. 35 is a diagram for explanation of the operation of the band limited image generating unit 601, and FIG. 36 shows a spatial frequency range of an ultrasonic image represented by image data DT(0) for one frame processed in the band limited image generating unit 601. In FIG. 36, the spatial frequency $f_0$ is the center frequency of the spatial frequency range of the ultrasonic image represented by image data DT(0).

As shown in FIG. 35, the image data DT(0) for one frame outputted from the primary memory 110 is subjected to thinning processing and filter processing such as Nyquist filter processing in a down-sampling unit 61. Thereby, down-sampling data LOW(0) having low spatial frequency components is generated.

Then, the down-sampling data LOW(0) is subjected to processing of inserting data of value "0" and filter processing such as smoothing filter processing in the up-sampling unit 62. Thereby, up-sampling data LOW(0)' having the same size as that of the original image data DT(0) is obtained. By performing processing of subtracting the up-sampling data LOW(0)' from the image data DT(0) in a subtracting unit 63, sub-band data SUB(1) is obtained.

Then, the sub-band data SUB(1) is subjected to thinning processing and predetermined filter processing in a down-sampling unit 64. Thus obtained down-sampling data SUB_LOW(0) is subjected to processing of inserting data of value "0" and filter processing such as smoothing filter processing in an up-sampling unit 65, thereby up-sampled so as to have the same size as that of the original image data. Thus obtained data BAND(1) is outputted as first band limited image data (OUTPUT 1). As shown in FIG. 36, the first band limited image data BAND(1) is image data representing an ultrasonic image with spatial frequencies limited to $f_0 \leq f \leq f_1$. Here, a spatial frequency $f_1$ is a center frequency in the frequency band $f \geq f_0$.

Furthermore, by performing processing of subtracting the data BAND(1) from the sub-band data SUB(1) in a subtracting unit 66, data BAND(2) is obtained. The data BAND(2) is outputted as second band limited image data (OUTPUT 2).

As shown in FIG. 36, the second band limited image data BAND(2) is image data representing an ultrasonic image with spatial frequencies limited to $f \leq f_1$.

In the embodiment, plural band limited images in which bands are not superimposed on one another can be generated by the processing.

Referring to FIG. 34 again, the band limited image analysis unit 602 analyzes band limited images represented by two kinds of band limited image data BAND(1) and BAND(2) generated in the band limited image generating unit 601.

Figure 37:
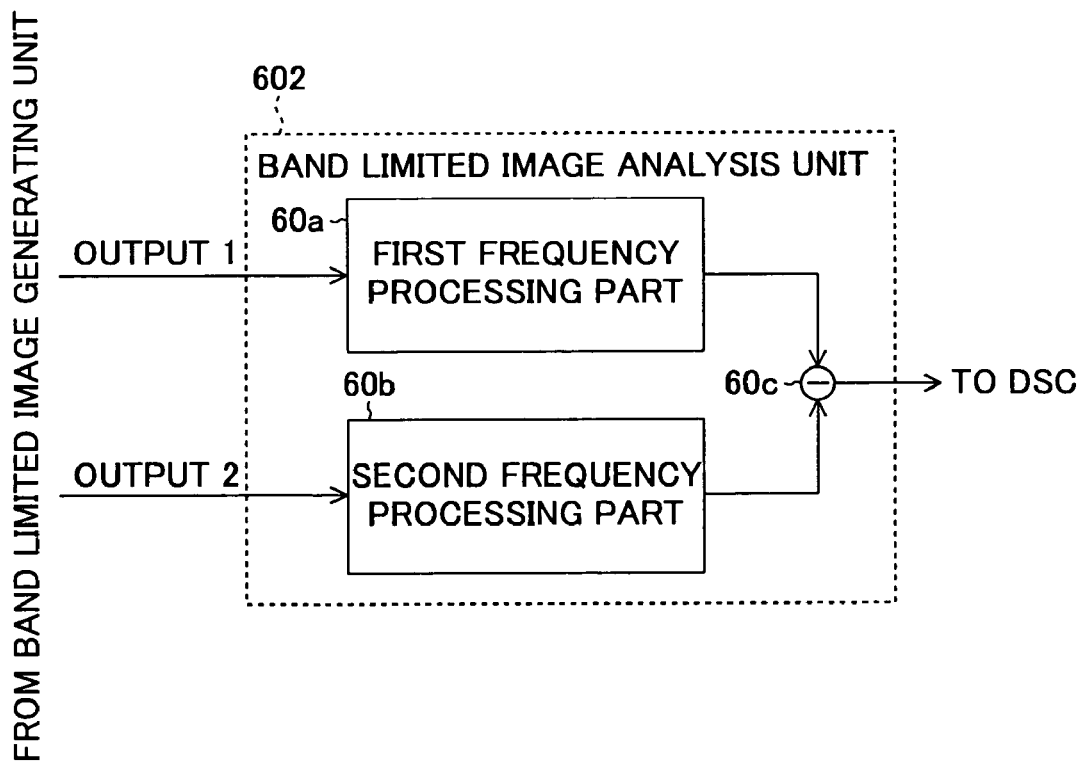
FIG. 37 is a block diagram showing a constitution of the band limited image analysis unit shown in FIG. 34.

FIG. 37 is a block diagram showing a constitution of the band limited image analysis unit 602. As shown in FIG. 37, the band limited image analysis unit 602 includes a first frequency processing part 60a, a second frequency processing part 60b and a subtraction part 60c.

The first frequency processing part 60a generates analysis data of the first band limited image by performing waveform/frequency transform processing on the first band limited image data BAND(1) (OUTPUT 1) outputted from the band limited image generating unit 601. On the other hand, the second frequency processing part 60b generates analysis data of the second band limited image by performing waveform/frequency transform processing on the second band limited image data BAND(2) (OUTPUT 2) outputted from the band limited image generating unit 601. The first and second frequency processing part 60a and 60b perform frequency processing that has been described by referring to FIGS. 10A-10C in the second embodiment. That is, a representative value (feature quantity) at time $t_0$ is obtained by performing FFT processing on signals for one line contained in the respective band limited image data. Thus obtained analysis data of first and second band limited images represent depth-dependent change of spatial frequency components contained in the respective band limited images.

The subtraction part 60c generates frequency difference data by performing subtraction between analysis data respectively outputted from the first and second frequency processing part 60a and 60b. The frequency difference data is outputted to the DSC 403 as band limited image analysis data.

Thus, the depth-dependent change of the intensity differences between the low frequency components and high frequency components contained in band limited images can be imaged by obtaining differences of analysis data based on the two kinds of band limited images in different bands.

Next, an ultrasonic imaging apparatus according to the thirteenth embodiment of the present invention will be described.

Figure 38:
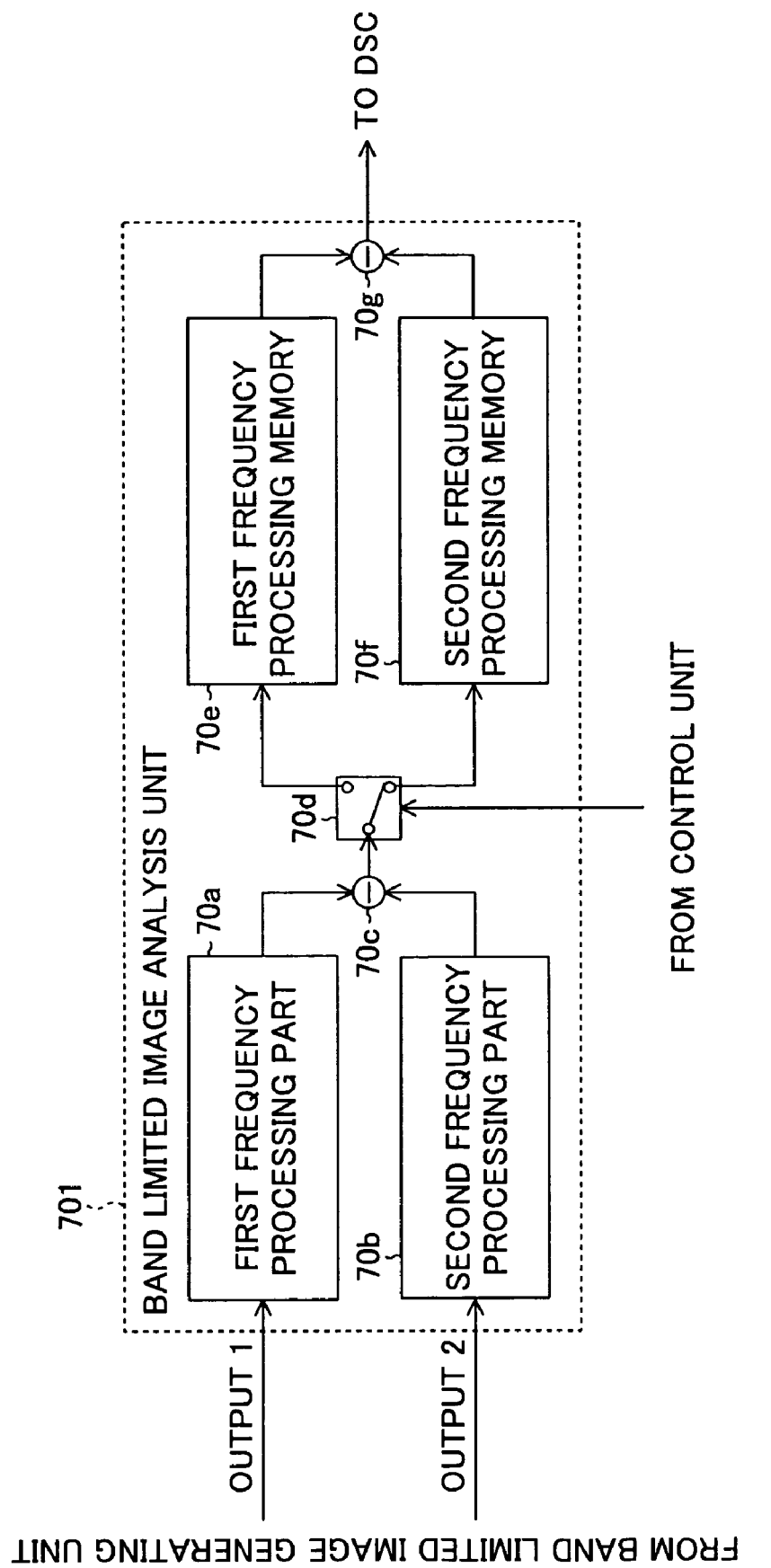
FIG. 38 is a block diagram showing a constitution of a band limited image analysis unit included in an ultrasonic imaging apparatus according to the thirteenth embodiment of the present invention.

The ultrasonic imaging apparatus according to the embodiment includes a band limited image analysis unit 701 as shown in FIG. 38 in place of the band limited image analysis unit 602 as shown in FIG. 34. Other constitution and operation are the same as those in the ultrasonic imaging apparatus as shown in FIG. 34.

As shown in FIG. 38, the band limited image analysis unit 701 includes a first processing part 70a, a second processing part 70b, a first subtraction part 70c, a switch 70d, a first frequency processing memory 70e, a second frequency processing memory 70f and a second subtraction part 70g. The constitution and operation of the first processing part 70a, the second processing part 70b and the first subtraction part 70c are the same as those of the first processing part 60a, the second processing part 60b and the subtraction part 60c as shown in FIG. 37, respectively.

The switch 70d selects one of output destinations of data from the subtraction part 70c under the control of the control unit 102 to allow the first frequency processing memory 70e and the second frequency processing memory 70f to alternately store frequency difference data for one frame sequentially outputted from the subtraction part 70c. The subtraction part 70g generates frame difference data by performing subtraction between frequency difference data respectively stored in those memories when the frequency difference data is updated in the first frequency processing memory 70e or the second frequency processing memory 70f. The frame difference data is outputted to the DSC 403 as band limited image analysis data.

Thus, by obtaining differences between frames of the two kinds of analysis data based on two band limited images in different bands, it becomes possible to obtain image data representing time-dependent change of the depth-dependent change of the intensity difference between the low frequency component and the high frequency component contained in the band limited images.

The invention claimed is:

1. An ultrasonic imaging apparatus for transmitting ultrasonic waves toward an object to be inspected and receiving ultrasonic echoes from the object to display an ultrasonic image based on the received ultrasonic echoes, said apparatus comprising:

ultrasonic transmitting and receiving means for transmitting ultrasonic waves according to applied drive signals, and receiving ultrasonic echoes reflected from the object to output reception signals;

signal processing means for performing signal processing on the reception signals outputted from said ultrasonic transmitting and receiving means to generate original data representing ultrasonic image information on the object;

speckle image generating means for generating speckle image data representing a speckle image based on the original data generated by said signal processing means;

speckle image analysis means for generating speckle analysis result image data representing a change of speckle images between adjacent two frames as a moving image based on the speckle image data generated by said speckle image generating means; and displaying means for displaying said analysis results represented by said speckle analysis result image data;

wherein said speckle image generating means generates structure image data based on at least one of (i) a first signal representing local maximum points extracted from the original data and interpolation points obtained by interpolation between the local maximum points, (ii) a second signal representing local minimum points extracted from the original data and interpolation points obtained by interpolation between the local minimum points, and (iii) a third signal representing average values of the first signal and the second signal, and generates the speckle image data by subtracting values represented by the structure image data from values represented by the original data.

2. An ultrasonic imaging apparatus according to claim 1, wherein said speckle image analysis means includes:

switch means for switching the speckle image data generated by said speckle image generating means frame by frame to output the speckle image data from a first output terminal and a second output terminal alternately;

a first storage unit for storing the speckle image data of one frame outputted from the first output terminal of said switch means;

a second storage unit for storing the speckle image data of another frame outputted from the second output terminal of said switch means; and difference calculating means for calculating differences between values of the speckle image data stored in said first storage unit and values of the speckle image data stored in said second storage unit.

3. An ultrasonic imaging apparatus according to claim 1, wherein:

said speckle image generating means includes a plurality of speckle image generating units for respectively generating plural pieces of speckle image data based on different frequency range components contained in the original data generated by said signal processing means; and said speckle image analysis means includes switch means for selecting one of the plural pieces of speckle image data generated by said plurality of speckle image generating units to output the selected speckle image data, and frequency processing means for performing frequency processing on the speckle image data outputted from said switch means.

4. An ultrasonic imaging apparatus according to claim 3, wherein said frequency processing means performs waveform/frequency transform processing on the speckle image data to obtain a space frequency distribution within a time window and a representative frequency of the space frequency distribution and converting an intensity at the representative frequency into a bright value while shifting the time window on each line.

5. An ultrasonic imaging apparatus according to claim 1, wherein:

said speckle image generating means includes a first speckle image generating unit for generating first speckle image data based on lower frequency components contained in the original data generated by said signal processing means, and a second speckle image generating unit for generating second speckle image data based on higher frequency components contained in the original data generated by said signal processing means; and said speckle image analysis means includes first frequency processing means for performing frequency processing on the first speckle image data generated by said first speckle image generating unit, second frequency processing means for performing frequency processing on the second speckle image data generated by said second speckle image generating unit, and difference calculating means for calculating differences between values of the first speckle image data on which frequency processing is performed by said first frequency processing means and values of the second speckle image data on which frequency processing is performed by said second frequency processing means.

6. An ultrasonic imaging apparatus according to claim 5, wherein each of said first and second frequency processing means performs waveform/frequency transform processing on the speckle image data to obtain a space frequency distribution within a time window and a representative frequency of the space frequency distribution and converting an intensity at the representative frequency into a bright value while shifting the time window on each line.

7. An ultrasonic imaging apparatus according to claim 1, wherein said speckle image generating means includes a plurality of speckle image generating units for respectively generating plural pieces of speckle image data based on different frequency range components contained in the original data generated by said signal processing means; and said speckle image analysis means includes first switch means for selecting one of the plural pieces of speckle image data generated by said plurality of speckle image generating units to output the selected speckle image data, frequency processing means for performing frequency processing on the speckle image data selected by said first switch means, second switch means for switching the speckle image data outputted from said frequency processing means frame by frame to output the speckle image data to two storage units alternately, and difference calculating means for calculating differences between values of the speckle image data stored in said two storage units frame by frame.

8. An ultrasonic imaging apparatus according to claim 7, wherein said frequency processing means performs waveform/frequency transform processing on the speckle image data to obtain a space frequency distribution within a time window and a representative frequency of the space frequency distribution and converting an intensity at the representative frequency into a bright value while shifting the time window on each line.

9. An ultrasonic imaging apparatus according to claim 1, wherein:
said speckle image generating means includes a first speckle image generating unit for generating first speckle image data based on lower frequency components contained in the original data generated by said signal processing means, and a second speckle image generating unit for generating second speckle image data based on higher frequency components contained in the original data generated by said signal processing means; and
said speckle image analysis means includes first frequency processing means for performing frequency processing on the first speckle image data generated by said first speckle image generating unit, second frequency processing means for performing frequency processing on the second speckle image data generated by said second speckle image generating unit, first difference calculating means for generating speckle image difference data by calculating differences between values of the first speckle image data on which frequency processing is performed by said first frequency processing means and values of the second speckle image data on which frequency processing is performed by said second frequency processing means, switch means for switching the speckle image difference data outputted from said first difference calculating means frame by frame to output the speckle image difference data to first storage unit and second storage unit alternately, and second difference calculating means for calculating differences between values of the speckle image difference data stored in said first storage unit and values of the speckle image difference data stored in said second storage unit.

10. An ultrasonic imaging apparatus according to claim 9, wherein each of said first and second frequency processing means performs waveform/frequency transform processing on the speckle image data to obtain a space frequency distribution within a time window and a representative frequency of the space frequency distribution and converting an intensity at the representative frequency into a bright value while shifting the time window on each line.

11. An ultrasonic imaging apparatus according to claim 1, wherein said speckle image generating means obtains a pixel value of an interpolation point by dividing an ultrasonic image into four two-dimensional areas with the interpolation point as a reference and performing four-point interpolation processing by employing one of four local maximum points, four local minimum points, and four average points of the respective local maximum points and the respective local minimum points, selected in the four two-dimensional areas.

12. An ultrasonic imaging apparatus according to claim 11, wherein said speckle image generating means selects one of the four local maximum points, the four local minimum points and the four average points by using square interpolation masks.

13. An ultrasonic imaging apparatus according to claim 11, wherein said speckle image generating means selects one of the four local maximum points, the four local minimum points and the four average points by using flat interpolation masks.

14. An ultrasonic imaging apparatus according to claim 11, wherein said speckle image generating means obtains a pixel value of the interpolation point by comparing pixel values based on one of the four local maximum points, the four local minimum points and the four average points selected by using square interpolation masks and pixel values based on one of the four local maximum points, the four local minimum points and the four average points selected by using flat interpolation masks.

15. An ultrasonic imaging apparatus according to claim 1, wherein said speckle image generating means obtains a pixel value of the interpolation point based on (i) pixel values of points selected from among the local maximum points, the local minimum points or the average points extracted from the original data and (ii) distances of the selected points and said interpolation point, or squares or third powers of the distances.

16. An ultrasonic imaging apparatus according to claim 1, further comprising:
operation means having a speckle analysis mode button for activating at least one of said speckle image generating means and said speckle image analysis means.

17. An ultrasonic imaging apparatus according to claim 16, wherein:
said operation means further has a control button to be used by an operator to select an image to be displayed on a screen from among a speckle image represented by the speckle image data and a speckle analysis result image represented by the speckle analysis result image data; and
said apparatus further comprises image selection means for selecting image data representing the image selected by the operator by using said control button to output the selected image data.

18. An ultrasonic imaging apparatus according to claim 16, wherein:
said operation means further has a control button to be used by an operator to select a size of the original image and the speckle analysis result image; and
said apparatus further comprises image synthesizing means for generating a side-by-side image in which the original image represented by the original data and the speckle analysis result image represented by the speckle analysis result image data are arranged in the size selected by the operator by using said control button.

19. An ultrasonic image processing apparatus for processing reception signals, which are obtained by transmitting ultrasonic waves toward an object to be inspected and receiving ultrasonic echoes from the object, to generate ultrasonic image data, said apparatus comprising:
speckle image generating means for generating speckle image data representing a speckle image based on original data generated by performing signal processing on the reception signals and representing ultrasonic image information on the object;

speckle image analysis means for generating speckle analysis result image data representing a change of speckle images between adjacent two frames as a moving image based on the speckle image data generated by said speckle image generating means; and displaying means for displaying said analysis results represented by said speckle analysis result image data;

wherein said speckle image generating means generates structure data based on at least one of (i) a first signal representing local maximum points extracted from the original data and interpolation points obtained by interpolation between the local maximum points, (ii) a second signal representing local minimum points extracted from the original data and interpolation points obtained by interpolation between the local minimum points, and (iii) a third signal representing average values of the first signal and the second signal, and generates the speckle image data by subtracting values represented by the structure image data from values represented by the original data.

20. An ultrasonic image processing method of processing reception signals, which are obtained by transmitting ultrasonic waves toward an object to be inspected and receiving ultrasonic echoes from the object, to generate ultrasonic image data, said method comprising the steps of:

(a) generating speckle image data representing a speckle image based on original data generated by performing signal processing on the reception signals and representing ultrasonic image information on the object;

(b) generating speckle analysis result image data representing a change of speckle images between adjacent two frames as a moving image based on the speckle image data generated at step (a); and (c) displaying said analysis results represented by said speckle analysis result image data;

wherein step (a) includes generating structure image data based on at least one of (i) a first signal representing local maximum points extracted from the original data and interpolation points obtained by interpolation between the local maximum points, (ii) a second signal representing local minimum points extracted from the original data and interpolation points obtained by interpolation between the local minimum points, and (iii) a third signal representing average values of the first signal and the second signal, and generating the speckle image data by subtracting values represented by the structure image data from values represented by the original data.

21. An ultrasonic image processing method according to claim 20, wherein step (b) includes calculating differences between values of the speckle image data in adjacent two frames generated at step (a).

22. An ultrasonic image processing method according to claim 20, wherein:

step (a) includes generating plural kinds of speckle image data based on different frequency band components contained in the original data; and step (b) includes selecting one of the plural kinds of speckle image data generated at step (a) and performing waveform/frequency transform processing on the selected speckle image data.

23. An ultrasonic image processing method according to claim 20, wherein:

step (a) includes generating first speckle image data based on lower frequency components contained in the original data and generating second speckle image data based on higher frequency components contained in the original data; and step (b) includes performing waveform/frequency transform processing on the first and second speckle image data and calculating differences between values of the processed first speckle image data and values of the processed second speckle image data.

24. An ultrasonic image processing method according to claim 20, wherein:

step (a) includes generating plural kinds of speckle image data based on different frequency band components contained in the original data; and step (b) includes selecting one of the plural kinds of speckle image data generated at step (a), performing waveform/frequency transform processing on the selected speckle image data, and calculating differences between values of the processed speckle image data in adjacent two frames.

25. An ultrasonic image processing method according to claim 20, wherein:

step (a) includes generating first speckle image data based on lower frequency components contained in the original data and generating second speckle image data based on higher frequency components contained in the original data; and step (b) includes performing waveform/frequency transform processing on the first and second speckle image data, generating speckle image difference data by calculating differences between values of the processed first speckle image data and values of the processed second speckle image data, and calculating differences between values of the speckle image difference data in adjacent two frames.

26. An ultrasonic image processing program, embodied in non-transitory form on a computer readable medium, for processing reception signals, which are obtained by transmitting ultrasonic waves toward an object to be inspected and receiving ultrasonic echoes from the object, to generate ultrasonic image data, said program actuating a CPU to execute the procedures of:

(a) generating speckle image data representing a speckle image based on original data generated by performing signal processing on the reception signals and representing ultrasonic image information on the object;

(b) generating speckle analysis result image data representing a change of speckle images between adjacent two frames as a moving image based on the speckle image data generated at procedure (a); and (c) providing said speckle analysis result image data generated at procedure (b) to a displaying device;

wherein procedure (a) includes generating structure image data based on at least one of (i) a first signal representing local maximum points extracted from the original data and interpolation points obtained by interpolation between the local maximum points, (ii) a second signal representing local minimum points extracted from the original data and interpolation points obtained by interpolation between the local minimum points, and (iii) a third signal representing average values of the first signal and the second signal, and generating the speckle image data by subtracting values represented by the structure image data from values represented by the original data.

27. An ultrasonic image processing program according to claim 26, wherein procedure (b) includes calculating differences between values of the speckle image data in adjacent two frames generated at procedure (a).

28. An ultrasonic image processing program according to claim 26, wherein:

procedure (a) includes generating plural kinds of speckle image data based on different frequency band components contained in the original data; and procedure (b) includes selecting one of the plural kinds of speckle image data generated at procedure (a) and performing waveform/frequency transform processing on the selected speckle image data.

29. An ultrasonic image processing program according to claim 26, wherein:

procedure (a) includes generating first speckle image data based on lower frequency components contained in the original data and generating second speckle image data based on higher frequency components contained in the original data; and procedure (b) includes performing waveform/frequency transform processing on the first and second speckle image data and calculating differences between values of the processed first speckle image data and values of the processed second speckle image data.

30. An ultrasonic image processing program according to claim 26, wherein:

procedure (a) includes generating plural kinds of speckle image data based on different frequency band components contained in the original data; and procedure (b) includes selecting one of the plural kinds of speckle image data generated at procedure (a), performing waveform/frequency transform processing on the selected speckle image data, and calculating differences between values of the processed speckle image data in adjacent two frames.

31. An ultrasonic image processing program according to claim 26, wherein:

procedure (a) includes generating first speckle image data based on lower frequency components contained in the original data and generating second speckle image data based on higher frequency components contained in the original data; and procedure (b) includes performing waveform/frequency transform processing the first and second speckle image data, generating speckle image difference data by calculating differences between values of the processed first speckle image data and values of the processed second speckle image data, and calculating differences between values of the speckle image difference data in adjacent two frames.

* * * * *